United States Patent
Fisker et al.

(10) Patent No.: US 10,456,229 B2
(45) Date of Patent: Oct. 29, 2019

(54) SCANNING OF EDENTULOUS PATIENTS

(71) Applicant: 3SHAPE A/S, Copenhagen K (DK)

(72) Inventors: Rune Fisker, Virum (DK); Lars Henriksen, Bagsvaerd (DK); Kristian Evers Hansen, Copenhagen Ø (DK)

(73) Assignee: 3SHAPE A/S, Copenhagen K (DK)

( * ) Notice: Subject to any disclaimer, the term of this patent is extended or adjusted under 35 U.S.C. 154(b) by 212 days.

(21) Appl. No.: 15/309,820

(22) PCT Filed: May 7, 2015

(86) PCT No.: PCT/EP2015/060086
§ 371 (c)(1),
(2) Date: Nov. 9, 2016

(87) PCT Pub. No.: WO2015/169910
PCT Pub. Date: Nov. 12, 2015

(65) Prior Publication Data
US 2017/0265977 A1 Sep. 21, 2017

(30) Foreign Application Priority Data
May 9, 2014 (DK) .................. 2014 70279

(51) Int. Cl.
*A61C 19/05* (2006.01)
*A61C 9/00* (2006.01)
(Continued)

(52) U.S. Cl.
CPC .............. *A61C 19/05* (2013.01); *A61C 9/004* (2013.01); *A61C 11/00* (2013.01); *A61C 11/006* (2013.01); *A61C 13/0001* (2013.01)

(58) Field of Classification Search
CPC ......... A61C 19/05; A61C 9/004; A61C 11/00; A61C 11/006; A61C 13/0001; A61C 13/0004
(Continued)

(56) References Cited

U.S. PATENT DOCUMENTS 6,259,943 B1 * 7/2001 Cosman ................ A61B 90/10
600/417
7,747,418 B2 * 6/2010 Leu ....................... A61C 8/0048
345/418
(Continued)

FOREIGN PATENT DOCUMENTS

| EP | 1 982 652 A1 | 10/2008 |
|---|---|---|
| JP | 2006-192223 A | 7/2008 |
| WO | WO 2012/083959 A1 | 6/2012 |

OTHER PUBLICATIONS

International Search Report (PCT/ISA/210) dated Jul. 28, 2015, by the European Patent Office as the International Searching Authority for International Application No. PCT/EP2015/060086.
(Continued)

*Primary Examiner* — Heidi M Eide
*Assistant Examiner* — Mirayda A Aponte
(74) *Attorney, Agent, or Firm* — Buchanan Ingersoll & Rooney P.C.

(57) ABSTRACT

Disclosed is a method for determining the relative arrangement of patient's jaws in a bite position when the patient's occlusion is not defined by natural teeth alone, where the method includes a step of obtaining a digital 3D representation including both surface data relating to dental tissue in one of the patient's jaws and surface data relating to a scan appliance arranged in relation to the jaw, where the scan appliance is configured for at least partly defining the patient's occlusion.

21 Claims, 12 Drawing Sheets

(51) Int. Cl.
*A61C 11/00* (2006.01)
*A61C 13/107* (2006.01)

(58) Field of Classification Search
USPC .......................... 433/68; 700/97, 98
See application file for complete search history.

(56) References Cited

U.S. PATENT DOCUMENTS

| | | | | |
|---|---|---|---|---|
| 2002/0081554 A1* | 6/2002 | Marshall | ............ | A61C 11/001 433/213 |
| 2004/0172150 A1* | 9/2004 | Perot | ................ | A61C 9/004 700/98 |
| 2006/0072810 A1* | 4/2006 | Scharlack | ........ | A61C 13/0004 382/154 |
| 2007/0190492 A1* | 8/2007 | Schmitt | ............ | A61C 13/0004 433/213 |
| 2008/0002869 A1 | 1/2008 | Scharlack et al. | | |
| 2011/0059413 A1* | 3/2011 | Schutyser | ............ | A61B 5/1077 433/8 |
| 2011/0060558 A1* | 3/2011 | Pettersson | .......... | A61B 17/8685 703/1 |
| 2012/0230567 A1* | 9/2012 | Greenberg | ............... | A61B 6/14 382/131 |
| 2012/0282567 A1* | 11/2012 | Nilsson | ............ | A61C 13/0004 433/68 |
| 2014/0242540 A1* | 8/2014 | Jones | .................... | A61C 9/00 433/71 |
| 2014/0372084 A1* | 12/2014 | Cowburn | ............ | A61C 9/0053 703/1 |

OTHER PUBLICATIONS

Written Opinion (PCT/ISA/237) dated Jul. 28, 2015, by the European Patent Office as the International Searching Authority for International Application No. PCT/EP2015/060086.

* cited by examiner

100

┌─────────────────────────────────────┐
│ Obtaining a first digital 3D representation
│ comprising surface data relating to dental
│ tissue in a first one of the patient's jaws │ 101
└─────────────────────────────────────┘
              ↓
┌─────────────────────────────────────┐
│ Obtaining a second digital 3D
│ representation comprising surface data
│ relating to dental tissue in a second one of
│ the patient's jaws │ 102
└─────────────────────────────────────┘
              ↓
┌─────────────────────────────────────┐
│ Arranging a first part of a scan appliance
│ at the first one of the jaws │ 103
└─────────────────────────────────────┘
              ↓
┌─────────────────────────────────────┐
│ Obtaining a third digital 3D representation
│ comprising both surface data relating to the
│ dental tissue in the first one of the patient's
│ jaws and surface data relating to the first
│ part of the scan appliance │ 104
└─────────────────────────────────────┘
              ↓
┌─────────────────────────────────────┐
│ Obtaining a fourth digital 3D representation
│ comprising surface data of the first part of
│ the scan appliance and surface data
│ relating to an opposing structure at the
│ second one of the jaws │ 105
└─────────────────────────────────────┘
              ↓
┌─────────────────────────────────────┐
│ Deriving one or more transformations for
│ mapping the first and second digital 3D
│ representations into the same coordinate
│ system. │ 106
└─────────────────────────────────────┘

FIG. 1A

SCANNING OF EDENTULOUS PATIENTS

TECHNICAL FIELD

This invention generally relates to a method for determining the relative arrangement of patient's jaws in a bite position when the patient's occlusion is not defined by natural teeth alone. More particularly, the invention relates to method comprising intra-oral scanning the patient with a scan appliance, such as a denture comprising openings, arranged in relation to the patient's jaw or jaws where the scan appliance least partly defines the patient's occlusion.

BACKGROUND

For a patient having his natural teeth in both jaws the occlusion and the relative arrangement of the jaws in occlusion are defined by these natural teeth. Some patients are missing teeth to an extent where the occlusion no longer can be defined by the natural teeth alone. This may be the case for a patient having at least one completely edentulous jaw. It may also be the case for a patient where some teeth are present but the antagonist teeth are not present.

A denture is a prosthetic device used for replacing teeth of an edentulous patient. The denture has a number of denture teeth and a base part preferably shaped and colored to mimic the patient's gum to provide the most aesthetic correct appearance. The base part of a conventional denture is configured for contacting the dental tissue of the jaw in such a manner that the conventional denture is attached to the jaw by suction. Attaching by suction provides that the denture is removable but also that it may unintentionally be release from the jaw. An alternative to a conventional denture is an implant-supported denture where the denture is fixated to the patient's jaw bone via implants secured in the jaw bone. This provides that the denture is held firmly in the correct position in the patient's mouth.

For a patient wearing a denture at a first one of the jaws, the occlusion can be defined by the denture teeth in collaboration with either teeth of a denture arranged at the opposing second one of the jaws or natural or implant supported teeth of the second one of the jaws.

The relative arrangement of an edentulous patient's jaws in a bite situation depends on the design of the denture. If e.g. the height of the denture teeth or denture base is increased, the corresponding jaw is moved further away from the occlusal plane and the other jaw.

When a patient has been wearing a conventional denture for a while and has found that its design provides a good and pleasant jaw motion during a bite he may wish that the relative arrangement of the jaws in the denture defined occlusion is transferred to a new denture, such as to a new implant based denture.

Intra-oral scanning of e.g. a completely edentulous patient without dentures can provide digital 3D representations comprising surface data relating to the gum tissue in the patient's jaws. Arranging the dentures in the mouth and scanning with the denture teeth in occlusion can provide a so-called bite scan which provides information relation to the relative arrangement of the dentures of the upper and lower jaw in occlusion. However this approach provides no information of the relative arrangement of the dentures and the jaws/the dental tissue of the jaws.

It thus remains a problem to provide a method for determining the relative arrangement of patient's jaws in a bite position when the patient's occlusion is not defined by the patient's natural teeth alone.

SUMMARY

Disclosed is hence a method for determining the relative arrangement of a patient's jaws in a bite position when the patient's occlusion is not defined by natural teeth alone, the method comprising:
  obtaining a first digital 3D representation comprising surface data relating to dental tissue in a first one of the patient's jaws;
  obtaining a second digital 3D representation comprising surface data relating to dental tissue in a second one of the patient's jaws;
  obtaining a third digital 3D representation comprising both surface data relating to the dental tissue in the first one of the patient's jaws and surface data relating to a first part of a scan appliance arranged in relation to the first one of the jaws, where the first part of the scan appliance is configured for at least partly defining the patient's occlusion in collaboration with an opposing structure at the second one of the jaws;
  obtaining a fourth digital 3D representation comprising surface data of the first part of the scan appliance and surface data relating to the opposing structure; and
  deriving one or more transformations for mapping the first and second digital 3D representations into the same coordinate system with a relative arrangement according to the relative arrangement of the jaws in the bite position.

One advantage of this method is that it allows for determining the relative arrangement of a patient's jaws in a bite position when the patient's occlusion is not defined by natural teeth alone. When the occlusion at least partly is defined by a scan appliance, such as by a maxillary and/or mandibular denture, the method provides that the relative arrangement of the jaws in the bite position can be determined.

The relative arrangement of the patient's jaws is described by the derived transformations which when applied to the first and/or second digital 3D representations provide that these are arranged in a coordinate system according to the relative arrangement of the patient's jaws in the bite position. Hence the relative arrangement of the first and second jaws in the bite position has been determined when the transformations are derived.

The method can provide a data file comprising surface data of dental tissue in a patient's jaws and information expressing the relative arrangement of the jaws in a bite position when the patient's occlusion is not defined by natural teeth alone. The derived transformations provide this information which together with at least the first and second digital 3D representations provides what is necessary to describe the relative arrangement of the jaws in the bite position defined by the scan appliance.

The transformations are configured to provide that when the first and second digital 3D representations are mapped into the same coordinate system by applying the derived transformations to the digital 3D representations, the dental tissue surface data comprised in these digital 3D representations are arranged according to their relative arrangement in a bite position of the patient's jaws. I.e. the relative arrangement of the patient's first and second jaws in the bite position has been determined.

When the first and second digital 3D representations are mapped into the same coordinate system using the disclosed method the dental tissue surface data of the first and second digital 3D representations are arranged according to their relative arrangement in to the bite.

It is an advantage that the third digital 3D representation comprises both surface data relating to the dental tissue in the first one of the patient's jaws and surface data relating to the first part of a scan appliance since this provides information about the relative arrangement of the first part of the scan appliance and the dental tissue of the first one of the jaws, i.e. about the position of the surface of the scan appliance relative to the surface of the dental tissue of the first jaw.

In the context of the present application, the phrase "the occlusion is not defined by natural teeth" refers to the situation where a number of the patient's teeth are missing such that the occlusion cannot be determined by his natural teeth or e.g. implant based teeth alone. This is for instance the case when the patient has a completely edentulous jaw.

With respect to defining the patient's occlusion an implant supported tooth can have the same function as a naturel tooth. Both are fixated to the patient's jaw bone and can participate in the defining of the occlusion.

In the context of the present application, the phrase "edentulous" is used both in relation to a partly edentulous patient having some teeth and in relation to completely edentulous patient's having no teeth. The phrase is hence also used in relation to both a partially and a completely edentulous jaw.

Determining the relative arrangement of a patient's jaws may comprise determining the arrangement of the dental tissue of the upper jaw relative to that of the lower jaw in the bite position defined by the scan appliance.

Unless otherwise explicitly stated the phrase "bite position" refers to the relative position of the patient's jaws in a bite defined at least partly by the scan appliance.

In the context of the present application, the phrase "mapping the first and second digital 3D representations into the same coordinate system" refers to the situation where it is provided that both digital 3D representations are expressed in a common coordinate system according to the correct relative arrangement of the patient's jaws in the bite position. One of the digital 3D representations may be fixed during the mapping such that the mapping, i.e. the transformations for mapping, not necessarily are applied to the dental tissue surface data of that digital 3D representation.

If a digital 3D representation of a section of an object and a digital 3D representation of the entire object are mapped into the same coordinate system the result is that the surface data for this section provided in the two digital 3D representations are aligned in the common coordinate system. The mapping can then be realized by determining a transformation which provides that the surface data of the two digital 3D representations relating to this section are aligned. The transformation may be determined by an iterative process such as by the Iterative Closest Point (ICP) algorithm where the distance between portions of two digital 3D representations relating to the same surface is minimized. The result of this algorithm is a transformation that when applied to one of these digital 3D representations provides that the two digital 3D representations are arranged in the common coordinate system with their data corresponding to the section aligned. When used in relation to the first and the third digital 3D representations such a transformation provides that the first and third digital 3D representations are digitally arranged according to the relative arrangement of the first scan appliance in relation to the dental tissue of the first one of the jaws.

In the present application the patient's occlusion is at least partly defined by a first part of the scan appliance in collaboration with an opposing structure at the second one of the jaws or by a single-piece scan appliance which engages both jaws and support these in an arrangement according to a bite position. When using a single-piece scan appliance this is referred to as the first part of the scan appliance.

When the opposing structure comprises natural teeth or implant supported teeth of the second one of the jaws, the first part of the scan appliance engages these natural or implant based teeth in the bite position of the jaws. The first part of the scan appliance in collaboration with these teeth then defines the occlusion. These teeth may then form part of the dental tissue of the second jaw which the second digital 3D representation comprises surface data for. In this case the surface data of the fourth digital 3D representation relating to the opposing structure and the dental tissue surface data of the second digital 3D representation may at least partly relate to the same physical surface, i.e. the surface of the teeth in the second one of the jaws.

If natural teeth also are missing in the second one of the jaws a second part of the appliance can be arranged at the second jaw. The second part of the scan appliance may then form part of the opposing structure, such that the first and second parts of the scan appliance engage each other in the bite position and thereby defines the patient's occlusion. The opposing structure is then at least partly defined by the second part of the scan appliance arranged in relation to the second one of the patient's jaws.

An existing denture or a try-in denture often cover the parts of the dental tissue of a jaw which can be used for mapping digital 3D representations of the denture and of the dental tissue below into the same coordinate system. Accordingly a digital 3D representation obtained e.g. by intra-oral scanning with a denture arranged at the patient's jaw has no surface data relating to this dental tissue.

In some embodiments, the first part of the scan appliance comprises one or more openings through which the dental tissue surface data can be recorded from the first one of the jaws. I.e. surface data relating to the dental tissue otherwise hidden by the scan appliance can be recorded while the first part of the scan appliance is placed at the first one of the jaws. An opening defined in the teeth part of a denture can e.g. provide access to the region of the alveolar ridge located at the hole. This provides that the third digital 3D representation can have surface data for the dental tissue of the first one of the jaws.

In some embodiments, the dental tissue surface data of the third digital 3D representation is recorded through one or more openings of the first part of the scan appliance, i.e. the surface data relating to the dental tissue in the first one of the patient's jaws is recorded through the openings of the first part of the scan appliance. The openings defined in a part of the scan appliance preferably provide visual access to the dental tissue of the corresponding jaws which otherwise would covered by the scan appliance.

It is advantageous that openings in the scan appliance provides visual access to the dental tissue since this allows the passage of light from an intra-oral scanner to the dental tissue and vice versa such that the scanner can record digital 3D representations comprising surface data relating to the dental tissue and surface data relating to the scan appliance.

In some embodiments at least one of the openings is defined by removing material of the scan appliance, such as by drilling.

When the scan appliance e.g. is an existing denture or a try-in denture, holes can be drilled at the clinic and the dentist can immediately scan the patient with the defined openings allowing the obtained third digital 3D representation to comprise both surface data relating to the denture and the portions of the underlying dental tissue arranged where the openings are defined.

In some embodiments the one or more openings comprise at least one aperture and/or at least one slit.

In the lower jaw the openings of the scan appliance may be arranged over the patient's arch, i.e. over teeth or gum surface situated in the arch below the scan appliance.

This is advantageous since aligning digital 3D representations based on surface data relating to the dental tissue below the tongue is difficult.

Digitally aligning e.g. the first and third digital 3D representations based on surface data relating to the dental tissue in the alveolar ridge of the lower jaw is hence often preferred.

In some embodiments, at least one of the transformations comprises one or more transformation matrices.

The one or more transformation matrices are then configured for bringing the digital 3D representations into the same coordinate system. A method for mapping the first and second digital 3D representations into the same coordinate system based on surface data of the third and fourth digital 3D representations may thus comprise determining such transformation matrices based on surface data of the third and fourth digital 3D representations.

The disclosed method is then for determining transformation matrices configured for digitally arranging dental tissue surface data of the first and second digital 3D representations of the patient's jaw according to a bite position of the patient.

The surface data of a digital 3D representation of an object describe the geometry of a surface of the object. For example the surface data relating to teeth in the second one of the patient's jaws describe the geometrical shape of a least part of these teeth.

The surface data of a digital 3D representation or the digital 3D representation itself may comprise a point cloud, a polygon or a triangle mesh.

The first digital 3D representation may be recorded using an intra-oral scanner without the first part of the scan appliance arranged in the patient's mouth such that there is visual access to the dental tissue of the first one of the jaws.

The second digital 3D representation may be obtained using an intra-oral scanner recording the surface data of the dental tissue of the second one of the patient's jaws. If the patient has both a maxillary and mandibular denture the denture at the second one of the jaws is preferably removed before recording the second digital 3D representation.

Scanning without a scan appliance at the jaw provides that surface data relating to e.g. the alveolar ridge can be comprised in the recorded digital 3D representation. This may be advantageous e.g. when an implant bar is to be designed for the attachment of an implant bar-supported denture in the patient's mouth or when a conventional denture is designed for the patient.

The first part of the scan appliance is arranged at the first one of the jaws while recording the third digital 3D representation using e.g. an intra-oral scanner. In addition to describing the geometry of the first part of the scan appliance and of the visible dental tissue (of the first one of the jaws), information of the relative arrangement of the dental tissue and the scan appliance part can also be derived from these surface data. This information provides that the third digital 3D representation can be used for determining the spatial relationship between the dental tissue surface data of the first digital 3D representation and the scan appliance surface data of the third digital 3D representation.

The first digital 3D representation often comprises surface data for a larger portion of the dental tissue than the third digital 3D representation. In some embodiments, the third digital 3D representation comprises dental tissue surface data for a portion of the dental tissue for which the first digital 3D representation comprises surface data.

The fourth digital 3D representation is obtained while the first part of the scan appliance is arranged at the first one of the patient's jaws and the jaws are arranged according to the bite position defined at least partly by the scan appliance. In the bite, the first part of the scan appliance is in occlusion with the opposing structure at the second one of the patient's jaws.

When the opposing structure comprises natural teeth or implant fixated teeth in the second one of the jaws, the first part of the scan appliance engages these teeth when the patient's jaws are arranged according to his bite, i.e. in occlusion. The fourth digital 3D representation then comprises surface data of both the first part of the scan appliance and the teeth (dental tissue) of the second one of the jaws, such that the fourth digital 3D representation provides information of the relative arrangement of the first part of the scan appliance and the teeth of the second one of the jaws in the bite position. The part of the fourth digital 3D representation relating to the opposing structure may then comprise surface data for portions of the second jaw teeth for which surface data also are provided in the second digital 3D representation. In other words, the dental tissue of the second jaw and the opposing structure can be the same physical units. The phrase "fourth digital 3D representation comprising surface data of the first part of the scan appliance and surface data relating to the opposing structure" may then refer to the case where the fourth digital 3D representation comprises surface data of the first part of the scan appliance and surface data relating to the teeth of the second one of the jaws.

In some cases the opposing structure at the second one of the jaws comprises a second part of the scan appliance and the first and second parts engage each other when the patient's jaw are arranged according to the bite position. The fourth digital 3D representation then comprises surface data of both the first and second parts of the scan appliance with these surface data expressing the relative arrangement of the first and second parts in the patient's bite.

The fourth digital 3D representation corresponds to a bite-scan, similar to a bite-scan for a patient in which his natural teeth define the occlusion.

In some cases, the steps of the procedure are performed at a dental clinic. In such cases the data of the digital 3D representations of the dental tissue and/or scan appliance are recorded at the dental clinic where also the subsequent analysis, such as aligning and mapping of surface data, is performed. In that context the phrase "obtaining a digital 3D representation" may relate to the situation where an electronic data file with the digital 3D representation is recorded by an intra-oral scanner and subsequently loaded into a data processing device, such as a computer system, comprising computer executable algorithms for the alignment and mapping of data and/or determining transformation matrices.

In some cases some steps of the procedure are performed at a dental clinic while others are performed at a remote location, such as at a dental lab.

In that context the phrase "obtaining a digital 3D representation" may relate to the situation where an electronic data file with the digital 3D representation received from the dental clinic is loaded into a computer system comprising computer executable algorithms for the alignment and mapping of data and/or determining transformation matrices.

In some embodiments, the opposing structure is at least partly defined by a second part of the scan appliance arranged in relation to the second one of the patient's jaws.

This is advantageous in cases where both jaws are edentulous to the extent that the opposing structure cannot be formed by natural or implant based teeth. The first and second parts then rest on the dental tissue of the first and second jaws, respectively, and collaborate to define the patient's occlusion without the help of natural teeth.

In some embodiments, the second part of the scan appliance comprises one or more openings through which dental tissue surface data for the second one of the jaws can be recorded.

In some embodiments, the method comprises obtaining a fifth digital 3D representation comprising both surface data relating to the dental tissue in the second one of the patient's jaws and surface data relating to the second part of the scan appliance.

The second part of the scan appliance is placed at the second one of the jaws while fifth digital 3D representation is recorded such that the fifth digital 3D representation describes arrangement of the second part of the scan appliance relative to the surface of the dental tissue of the second one of the jaws.

In some embodiments, the dental tissue surface data of the fifth digital 3D representation is recorded through the one or more openings of the second part of the scan appliance. The second part of the scan appliance is arranged at the second one of the jaws while recording the fifth digital 3D representation using e.g. an intra-oral scanner. In addition to describing the geometry of the second part of the scan appliance and of the visible dental tissue (of the second one of the jaws), information of the relative arrangement of the dental tissue and this scan appliance part can also be derived from these surface data. This information provides that the fifth digital 3D representation can be used for determining the spatial relationship between the dental tissue surface data of the second digital 3D representation and the scan appliance surface data of the fifth digital 3D representation.

The second digital 3D representation often comprises surface data for a larger portion of the dental tissue than the fifth digital 3D representation.

The coordinate system which the digital 3D representations are mapped into can be that of any of the first, second, third, fourth or fifth digital 3D representations, or in principle any other common coordinate system.

In some embodiments, the coordinate system into which the dental tissue surface data of the first and second digital 3D representations are mapped is the coordinate system of the fourth digital 3D representation.

This provides that the dental tissue surface data of the first and second digital 3D representations are expressed in the coordinates of the bite scan.

In some embodiments, the coordinate system into which the dental tissue surface data of the first and second digital 3D representations are mapped is the coordinate system of the second digital 3D representation. If the second one of the jaws e.g. is the lower jaw, the dental tissue surface data of the first and second digital 3D representations are then expressed in the coordinates of the lower jaw scan.

In some embodiments, the coordinate system into which the dental tissue surface data of the first and second digital 3D representations are mapped is the coordinate system of the first digital 3D representation. If the first one of the jaws e.g. is the upper jaw, the dental tissue surface data of the first and second digital 3D representations are then expressed in the coordinates of the upper jaw scan.

In some embodiments, a first one of the transformations is derived at least partly based on dental tissue surface data of the third digital 3D representation recorded through the one or more openings in the first part of the scan appliance and on the corresponding dental tissue surface data of the first digital 3D representation.

When applied to the first and/or third digital 3D representation the first transformation provides that the first and third digital 3D representations are mapped into a common coordinate system with their surface data relating to the dental tissue in the first jaw aligned. I.e. the surface data of the first and third digital 3D representations relating to this dental tissue are aligned. Further, the first transformation provides that the first and third digital 3D representations digitally are arranged according to the physical arrangement of the first part of the scan appliance relative to the dental tissue of the first one of the jaws.

I.e. the dental tissue surface data of the first digital 3D representation and the scan appliance surface data of the third digital 3D representation are digitally arranged according the physical reality in the patient's mouth when the scan appliance is arranged at the first on of the jaws.

The first transformation can be derived using an iterative algorithm e.g. the Iterative Closest Point (ICP) algorithm which provides a transformation for fitting one digital 3D representation to another fixed digital 3D representation. The iterative algorithm can e.g. be applied to the first digital 3D representation such that a dental tissue portion of the first digital 3D representation is aligned with a portion of the third digital 3D representation corresponding to the same dental tissue in the first one of the jaws.

In some embodiments the mapping, i.e. the mapping of the first and second digital 3D representations into the same coordinate system, comprises aligning the first and third digital 3D representations based on the dental tissue surface data comprised therein.

The first and third digital 3D representations comprise dental tissue surface data relating to the same dental tissue, such as dental tissue visible through openings in the scan appliance. This allows the first and third digital 3D representations to be digitally aligned using e.g. Iterative Closest Point (ICP) algorithms on these dental tissue surface data to determine e.g. a transformation $T_{1,3}$ configured for aligning the dental tissue surface data of the first digital 3D representation with the dental tissue surface data of the third digital 3D representation or a transformation $T_{3,1}$ configured for bringing the dental tissue and scan appliance surface data of the third digital 3D representation into the coordinate system of the first digital 3D representation with the corresponding dental tissue surface data aligned.

In some embodiments, a second one of the transformations is derived at least partly based on scan appliance surface data of the third and fourth digital 3D representations.

When applied to the third and/or fourth digital 3D representation the second transformation provides that the third and fourth digital 3D representations are arranged with aligned scan appliance surface data, i.e. surface data for the first part of the scan appliance comprised in the third and fourth digital 3D representation are aligned in a common coordinate system. The relative arrangement of the transformed third and/or fourth digital 3D representations describes the physical arrangement of the first part of the scan appliance relative to the opposing structure when the jaws are in the bite position. In some embodiments the mapping, i.e. the mapping of the first and second digital 3D representations into the same coordinate system, comprises aligning the third and fourth digital 3D representations based on the scan appliance surface data comprised therein.

The third and fourth digital 3D representations both comprise surface data relating to the first part of the scan appliance. This allows the third and fourth digital 3D representations to be digitally aligned using e.g. ICP algorithms to derive e.g. a transformation $T_{3,4}$ configured for bringing the scan appliance and dental tissue surface data of the third digital 3D representation into the coordinate system of the fourth digital 3D representation. This provides that dental tissue surface data of the third digital 3D representation (relating to the first one of the jaws) are expressed in the same coordinate system as the scan appliance surface data of the fourth digital 3D representation with the correct arrangement of the dental tissue data and the scan appliance surface data provided in the fourth digital 3D representation.

The algorithms may also be configured for deriving a transformation $T_{4,3}$ configured for bringing the surface data of the fourth digital 3D representation into the coordinate system of the third digital 3D representation.

Applying the transformations $T_{1,3}$ and $T_{3,4}$ to the dental tissue surface data of the first digital 3D representation provides that the surface data of the transformed first digital 3D representation are arranged relative to the surface data of the fourth digital 3D representation according to the relative arrangement of these surfaces in the bite position. In other words, the dental tissue surface data for the first one of the jaws (supplied in form of the first digital 3D representation) is expressed in coordinates of the "bite-scan".

Applying the transformations $T_{3,1}$ and $T_{4,3}$ to the surface data of the fourth digital 3D representation provides that the surface data of the transformed fourth digital 3D representation are arranged relative to the dental tissue surface data of the first digital 3D representation according to the relative arrangement of these surfaces in the bite position. Surface data of the fourth digital 3D representation relating to a second part of the scan appliance and/or dental tissue of the second one of the jaws then mapped into the coordinate system of the first digital 3D representation. In other words, the surface data describing the relative arrangement of the first part of the scan appliance and the opposing structure provided in the "bite scan" are expressed in coordinates of the first one of the jaws.

In some embodiments, a third one of the transformations is configured for transforming the second and/or the fourth digital 3D representations to provide that the relative arrangement of the surface data of the second and fourth digital 3D representations is according to the physical arrangement of the corresponding surfaces in the patient's mouth.

When the opposing structure comprises teeth in the second one of the jaws the third transformation may be directly derived from the second and fourth digital 3D representations, where the third transformation provides that at least part of the teeth surface data of the second digital 3D representation is aligned with the surface data of the fourth digital 3D representation corresponding to surfaces of the teeth in the second one of the jaws forming the opposing structure for the first part of the scan appliance.

In some embodiments, the third one of the transformations is configured to provide that at least part of the surface data of the second and fourth digital 3D representations relating to the teeth in the second one of the jaws are aligned. When applied to the fourth digital 3D representation the third transformation provides that the surface data of the fourth digital 3D representation relating to the teeth of the second one of the patient's jaws are aligned with the corresponding surface data of the second digital 3D representation in the same coordinate system as the second digital 3D representation.

The third transformation may be derived using a computer-implemented algorithm, such as the ICP-algorithm, which returns the transformation required for aligning dental tissue surface data of the second and fourth digital 3D representations.

When the second one of the jaws is edentulous, the effect of the third transformation is preferably to provide that dental tissue surface data of the second digital 3D representation relating to the gum of the second one of the jaws and the surface data of the fourth digital 3D representation relating to the second part of the scan appliance are arranged according to the relative arrangement of these surfaces when the second part of the appliance is placed at the second one of the jaws.

When the opposing structure comprises a second part of the scan appliance, such as a denture for the second one of the jaws, the third transformation may be derived via the fifth digital 3D representation.

In some embodiments, the third one of the transformations comprises a transformation configured for transforming the second and/or the fifth digital 3D representations to provide that the second and fifth digital 3D representations are arranged with aligned dental tissue surface data and a transformation configured for transforming the fourth and/or the fifth digital 3D representation to provide that the fourth and fifth digital 3D representations are arranged with aligned scan appliance surface data.

The transformation configured for transforming the second and/or the fifth digital 3D representations may be derived based on the surface data of the second and fifth digital 3D representations relating to the same dental tissue in the second one of the patient's jaws. This may be realized using an algorithm, such as the ICP algorithm, which derives a transformation for aligning dental tissue surface data of the fifth digital 3D representation with the corresponding dental tissue surface data of the second digital 3D representation or vice versa.

In some embodiments the mapping of the first and second digital 3D representations into the same coordinate system comprises aligning the dental tissue surface data of the second and fifth digital 3D representations.

The second and fifth digital 3D representations comprise dental tissue surface data relating to the same dental tissue of the second one of the jaws, such as the dental tissue which is visible through the an opening in the second part of the scan appliance. This allows the second and fifth digital 3D representations to be digitally arranged according to the physical arrangement of the second part of the scan appliance at the second one of the jaws based on an alignment of these dental tissue surface data. The alignment can be provided by or expressed as a transformation $T_{2,5}$ configured for transforming the second digital 3D representation such that its dental tissue surface data are aligned with the dental tissue surface data of the fifth digital 3D representation or the opposite situation where the alignment is provided by or expressed as a transformation $T_{5,2}$ configured for transforming the fifth digital 3D representation such that its dental tissue surface data are aligned with the dental tissue surface data of the second digital 3D representation. In both cases the dental tissue surface data of the second digital 3D representation can be thought as being expressed in the same coordinate system as the surface data of the fifth digital 3D representation, i.e. the scan appliance and dental tissue surface data of the fifth digital 3D representation. Such transformations can be determined using e.g. ICP algorithms that align the dental tissue surface data of the second and fifth digital 3D representations.

The transformation configured for transforming the fourth and/or the fifth digital 3D representations may be derived based on the surface data of the fourth and fifth digital 3D representations relating to the same portions of the second part of the scan appliance. This may be realized using an algorithm, such as the ICP algorithm, which derives a transformation for aligning scan appliance surface data of the fifth digital 3D representation with the corresponding surface data of the fourth digital 3D representation or vice versa.

In some embodiments the mapping of the first and second digital 3D representations into the same coordinate system comprises aligning the scan appliance surface data of the fourth and fifth digital 3D representations, i.e. aligning the surface data relating to the second part of the scan appliance.

The fourth and fifth digital 3D representations both comprise surface data relating to the second part of the scan appliance. This allows the fourth and fifth digital 3D representations to be digitally arranged according to the physical arrangement of the second part of the scan appliance relative to the first part of the scan appliance in the bite position based on an alignment of scan appliance surface data. The alignment can be provided by or expressed as a transformation $T_{5,4}$ configured for transforming the fifth digital 3D representation such that its scan appliance surface data are aligned with the surface data for the second part of the scan appliance of the fourth digital 3D representation or the opposite situation where the alignment is provided by or expressed as a transformation $T_{4,5}$ configured for transforming the fourth digital 3D representation such that its scan appliance surface data are aligned with the surface data for the second part of the scan appliance of the fifth digital 3D representation. In both cases the dental tissue surface data and scan appliance surface of the fifth digital 3D representation can be said to be expressed in the same coordinate system as the scan appliance surface data of the fourth digital 3D representation. Such transformations can be determined using e.g. ICP algorithms that align the scan appliance surface data of the fifth and fourth digital 3D representations.

Applying the transformations $T_{2,5}$ and $T_{5,4}$ to the second digital 3D representation provides that the dental tissue surface data of the transformed second digital 3D representation are arranged relative to the scan appliance surface data of the fourth digital 3D representation according to the relative arrangement of the corresponding surfaces in the bite position. The dental tissue surface data of the second digital 3D representation may then be said to be mapped into the coordinate system of the fourth digital 3D representation.

In other words, combining the alignment of surface data for corresponding surfaces in the second and fifth digital 3D representations and the alignment of surface data for corresponding surfaces in the fifth and fourth digital 3D representations provides that relative arrangement of the dental tissue surface data of the second jaw and surface data of the scan appliance has been determined. I.e. the arrangement of the surface data for the dental tissue in the second one of the jaws is relative to the "bite-scan" has been determined.

Applying the transformations $T_{4,5}$ and $T_{5,2}$ to the fourth digital 3D representation provides that the surface data of the transformed fourth digital 3D representation are arranged relative to the dental tissue surface data of the second digital 3D representation according to the relative arrangement of the corresponding surfaces in the bite position.

The surface data of the fourth digital 3D representation relating to the second part of the scan appliance may then be said to be mapped into the coordinate system of the second digital 3D representation, where the surface data of the fourth digital 3D representation expresses the relative arrangement of the first and second parts of the scan appliance in the bite position.

A workflow which determines both the relative arrangement of the first and fourth digital 3D representation (the bite scan) and of the second and fourth digital 3D representations in the bite position provides that the relative arrangement of the first and second digital 3D representations in the bite position is determined.

The relative arrangement of the first and second digital 3D representations can also be determined by determining the transformation which when applied to the first digital 3D representation provides that the transformed first digital 3D representation is arranged relative to the dental tissue surface data of the second digital 3D representation according to the relative arrangement of the first and second jaws in the bite position. This can be realized by applying the transformations $T_{5,2}\ T_{4,5}\ T_{3,4}\ T_{1,3}$ to at least the dental tissue surface data of the first digital 3D representation. Here the combined effect of $T_{3,4}$ and $T_{1,3}$ is to arrange the dental tissue surface data of the first digital 3D representation relative to the fourth digital 3D representation. From there the combined effect of $T_{5,2}\ T_{4,5}$ is to arrange the dental tissue surface data of the first digital 3D representation relative to the surface data of the second digital 3D representation. The dental tissue surface data of the first and second digital 3D representations are thereby arranged in a relative arrangement according to the arrangement of the patient's jaws in the occlusion defined by the first and second parts of the scan appliance. The relative arrangement of the jaws in a bite position where the occlusion is defined by the scan appliance has thus been determined.

In some cases, e.g. when the patient misses all teeth in the upper jaw but has some natural teeth or implant supported teeth in the lower jaw, these teeth may define the patient's occlusion in collaboration with the first part of the scan appliance arranged at the upper jaw, i.e. the opposing structure comprises teeth of the second one of the patient's jaws (here the lower jaw).

Preferably, the fourth digital 3D representation then also comprises dental tissue surface data relating to the teeth of the second one of the patient's jaws. This provides that the relative arrangement of the second and fourth digital 3D representations in the bite position can be determining by deriving the transformation which provides that the dental tissue surface data relating to these teeth is aligned.

In some embodiments, the opposing structure is at least partly defined by teeth of the second one of the patient's jaws, and at least part of the dental tissue surface data of the second and of the fourth digital 3D representations relate to the teeth of the second one of the patient's jaws.

In some embodiments the mapping, i.e. the mapping of the first and second digital 3D representations into the same coordinate system, comprises aligning the second and fourth digital 3D representations based on the surface data relating to the teeth of the second one of the patient's jaws.

In some embodiments deriving the transformation for mapping the first and second digital 3D representations into the same coordinate system comprises deriving a transformation which provides that the surface data relating to the teeth of the second one of the patient's jaws provided in the second and fourth digital 3D representations are aligned.

This allows the fourth and second digital 3D representations to be digitally aligned based on these dental tissue (teeth) surface data. The alignment can be provided by or expressed as a transformation $T_{2,4}$ configured for transforming the second digital 3D representation such that the dental tissue surface data of the transformed second digital 3D representation is aligned with the corresponding surface data of the fourth digital 3D representation or the opposite situation where the alignment is provided by or expressed as a transformation $T_{4,2}$ configured for transforming the fourth digital 3D representation such that the dental tissue surface data of the transformed fourth digital 3D representation is aligned with the corresponding surface data of the second digital 3D representation. In both cases the dental tissue surface data of the second digital 3D representation are expressed in the same coordinate system as the scan appliance surface data of the fourth digital 3D representation. Such transformation matrices can be determined using e.g. ICP algorithms that align the second and fourth digital 3D representations based on the dental tissue (teeth) surface data comprised therein.

When the transformation for mapping the dental tissue surface data of the first and second digital 3D representations into the same coordinate system the relative arrangement of the patient's jaws in the bite position defined by at least partly by the first part of the scan appliance is determined.

In a data file created at least partly by mapping the dental tissue surface data of the first and second digital 3D representations into a common coordinate system, the dental tissue surface data may be arranged according the surface of the dental tissue of the jaws in this bite position.

In some embodiments the scan appliance comprises a second part configured for engaging dental tissue of the second one of the patient's jaws.

The second part of the scan appliance may form the opposing structure that together with the first part defines the occlusion.

In some embodiments, the first and/or second parts of the scan appliance comprises portions configured for engaging dental tissue of the first and second one of the patient's jaws, respectively. For a completely edentulous jaw the corresponding part of the scan appliance is preferably configured for engaging the gum of that jaw. If a jaw is partly edentulous the scan appliance part for that jaw may be configured for engaging the teeth and/or the gum of that jaw.

In some embodiments the first and/or second parts of the scan appliance comprises a dental component selected from the group of:
  a denture,
  a copy of denture,
  a try-in denture, or
  a bite rim.

The denture can be a full or a partial denture.

The try-in denture may have been produced for testing a planned setup of the denture teeth.

In some embodiments, the first and second parts of the scan appliance comprise a first and a second denture, respectively.

This is advantageous e.g. for a completely edentulous patient who often has a maxillary denture for the upper jaw and a mandibular denture for the lower jaw. The first part of the scan appliance may then comprise the maxillary denture and the second part a mandibular denture, or vice versa.

In some embodiments, the first and the second denture form the first and second parts of the scan appliance, respectively.

For an edentulous patient the relative arrangement of the jaws in the bite often depends on the scan appliance. In cases where the scan appliance comprises a denture, the relative arrangement of the jaws in the bite depends on the design of this denture.

If for example the patient has a maxillary denture arranged at the upper jaw and all his natural teeth in the lower jaw, the natural teeth of the lower jaw and the denture teeth of the maxillary denture engage to define the patient's occlusion and the relative arrangement of the jaws in the bite position. The design of the maxillary denture then determines the relative arrangement of the gum of the upper jaw and the teeth of the lower jaw. If e.g. the height of the denture teeth and/or denture base is reduced the distance between the gum of the upper jaw and the teeth of the upper jaw is reduced.

In some cases the scan appliance can be a denture worn by the patient for years. The patient is perhaps pleased with the occlusion of the denture teeth but not with the aesthetic appearance of e.g. the teeth or the gum part of the denture. It may then advantageous to transfer the relative arrangement of the jaws in the bite position to the design of a new denture to the new denture while e.g. the teeth shade and the shape details on the gum part are modified.

The transfer may also be to a planning of an implant procedure or a design of an implant bar structure configured for supporting a new denture in the mouth.

The methods according disclosed herein provides this since the relative arrangement of the jaws in the patient's bite is determined.

In some embodiments, the first part of the scan appliance forms the scan appliance such that the scan appliance has no second part. This may for example be the case when patient has teeth in the second jaw forming the opposing structure.

In some embodiments, the scan appliance is a single-piece component where the first and second parts are integrated portions of the scan appliance.

In some embodiments, the scan appliance is a multi-piece component where the first and second parts are separate portions of the scan appliance.

In some embodiments, the first and second parts of the scan appliance are configured for mating with the dental tissue of the first and second one of the patient's jaws, respectively, and the scan appliance comprises a connecting part configured for at least temporarily supporting the first and second parts in an arrangement which expresses the patient's occlusion, and where the openings are defined in the first parts and/or in the second part and/or in the connecting portion.

The opposing structure may then comprise the second part and the connecting part of the scan appliance.

In some embodiments, the method comprises identifying portions of the third digital 3D representation relating to the first part of the scan appliance and identifying portions relating to the dental tissue in the first one of the patient's jaws, such as the portions relating to the dental tissue recorded though the one or more openings of the first part of the scan appliance.

In some embodiments, the method comprises identifying portions of the fifth digital 3D representation relating to the second part of the scan appliance and identifying portions relating to the dental tissue in the second one of the patient's jaws.

In some embodiments, at least the third and/or fifth digital 3D representation comprises color data in addition to the surface data describing the geometry of the dental tissue and scan appliance.

This provides the advantage that the surfaces of the scan appliance and the dental tissue can be distinguished if the color of the scan appliance differs from that of the dental tissue.

In some embodiments, the first and/or second part of the scan appliance has a color which differs from the colors of the patient's dental tissue and wherein the identifying comprises executing computer implemented algorithms configured for distinguishing between the scan appliance and the dental tissue based on color data of the third and/or fifth digital 3D representation. The scan appliance may e.g. be manufactured in a yellow, green, or blue material.

This provides for an automatic and hence fast identification of which portions of the digital 3D representations relate to the dental tissue and which relate to the scan appliance.

In some embodiments the identifying comprises digitally placing one or more sets of correlated digital alignment points on the third digital 3D representation and on the first digital 3D representation.

In some embodiments the identifying comprises digitally placing one or more sets of correlated digital alignment points on the second digital 3D representation and on the fifth digital 3D representation.

In order to align digital 3D representations of 3D structures at least three digital alignment points must be placed on the first digital 3D representation with a corresponding point on the third digital 3D representation. The same is true for the second and fifth digital 3D representations.

This allows an operator to identify which portions of the obtained digital 3D representations can be used for the alignment based on dental tissue surface data or scan appliance surface data. The digital alignment points may mark the center each portion or the digital alignment points may be formed as enclosed portions defined e.g. using a 3D spline.

In some embodiments at least the third digital 3D representation is obtained by intra-oral scanning of the patient with the first part of the scan appliance arranged in relation to the first one of the patient's jaws. The first part of the scan appliance is preferably formed such that the third digital 3D representation comprises surface data relating to the first part of the scan appliance and surface data relating to dental tissue of the first one of the patient's jaws.

In some embodiments at least the fifth digital 3D representation is obtained by intra-oral scanning of the patient with the second part of the scan appliance arranged in relation to the second one of the patient's jaws. The second part of the scan appliance is preferably formed such that the fifth digital 3D representation comprises surface data relating to the second part of the scan appliance and surface data relating to dental tissue of the second one of the patient's jaws.

In some embodiments, the dental tissue for which surface data is obtained in the first and third digital 3D representations comprises soft dental tissue of the first one of the patient's jaws.

The aligning of the first and third digital 3D representations can then be based on surface data relating to the soft dental tissue.

In some embodiments, the dental tissue for which surface data is obtained in the second and fifth digital 3D representations comprises soft dental tissue of second one of the patient's jaws.

The aligning of the second and fifth digital 3D representations can then be based on surface data relating to the soft dental tissue.

For a scan appliance arranged at the upper jaw, it may be advantageous to provide visual access to the patient's palette since this provides structure which is good for alignment of digital 3D representations. For a denture the visual access can be provided via openings arranged at the part of the scan appliance facing the palette. Also the gum at alveolar ridge can be used for this alignment and openings may be defined at a corresponding part of the scan appliance.

In some embodiments, the dental tissue for which surface data is obtained in the second digital 3D representations comprises hard dental tissue of the patient's upper or lower jaw, such as natural or implant-supported teeth of the upper or lower jaw.

This is for instance the case when all natural teeth are present in the second one of the jaws while a denture is arranged at the first one of the jaws.

The fourth digital 3D representation then preferably comprises surface data relating to the same portions of the hard dental tissue such that the second and fourth digital 3D representations can be aligned based on surface data relating to the teeth.

In some embodiments, the third and fourth digital 3D representations comprises surface data for a first and a second portion, respectively, of the first part of the scan appliance, where there may be no overlap between the first and second portions. Knowledge of the shape of the scan appliance, i.e. a digital 3D representation of the scan appliance, may then be used to link the third and fourth digital 3D representations. This can be done by registration of the third and fourth digital 3D representations of the digital 3D representation of the scan appliance.

The same is true for the fifth and the fourth digital 3D representation which may be linked via a digital 3D representation of the second part of the scan appliance.

Some teeth may also be present in the first one of the jaws such that the alignment of the first and third digital 3D representations at least partly can be based on surface data relating to these teeth.

The order in which the digital 3D representations are obtained is irrelevant and the second and third digital 3D representations can e.g. be obtained prior to obtaining the first digital 3D representations.

Disclosed is a scan appliance for use in determining the relative arrangement of patient's jaws in a bite position when the patient's occlusion is not defined by natural teeth alone, sad scan appliance comprising:
  a first part adapted for engaging dental tissue of a first one of the patient's jaws and for engaging an opposing structure at a second one of the patient's jaws,
where the scan appliance is configured for supporting the patient's jaws and at least partly defining the patient's occlusion.

In some embodiments, the scan appliance is configured for defining the patient's occlusion in collaboration with an opposing structure at the second one of the jaws In some embodiments, the first part of the scan appliance comprises one or more openings configured for providing visual access to underlying dental tissue of the first one of the jaws, said openings allowing that the surface data of the third digital 3D representation relating to the dental tissue in the first one of the patient's jaws can be recorded.

In some embodiments, the second part of the scan appliance comprises one or more openings configured for providing visual access to underlying dental tissue of the second one of the jaws, said openings allowing that the surface data of the fifth digital 3D representation relating to the dental tissue in the second one of the patient's jaws can be recorded.

The transformation of a digital 3D representation may be expressed by one or more transformation matrices configured for bringing surface data of the digital 3D representation into the same coordinate system as the surface data of the other digital 3D representation, e.g. to provide that surface data for a specific surface are aligned.

In some embodiments the mapping comprises determining transformation matrices configured for digitally arranging the dental tissue surface data of the first and second digital 3D representations according to the patient's occlusion, where at least one of said transformation matrices is configured for aligning the dental tissue surface data of the first and third digital 3D representations, and at least one of said transformation matrices is configured for aligning the scan appliance surface data of the third and fourth digital 3D representations.

Some of these transformation matrices may be configured to provide that when applied to the dental tissue surface data of the first digital 3D representation these surface data are mapped into the same coordinate system as the scan appliance surface data of the fourth digital 3D representation where they are arranged according to the arrangement of the patient's dental tissue relative to the scan appliance.

When a second part of the scan appliance is used for defining the occlusion, the fifth digital 3D representation may be obtained, where the fifth digital 3D representation comprises surface data relating to the second scan appliance and surface data relating to the dental tissue of the second one of the jaws. In such cases it may be relevant to determine transformation matrices for aligning the dental tissue surface data of the second and fifth digital 3D representations based on the fourth digital 3D representation.

Accordingly, in some embodiments at least one of said transformation matrices is configured for aligning the dental tissue surface data of the second and fifth digital 3D representations, and at least one of said transformation matrices is configured for aligning the scan appliance surface data of the fifth and fourth digital 3D representations.

Some of these transformation matrices may be configured to provide that when applied to the dental tissue surface data of the second digital 3D representation these surface data are mapped into the same coordinate system as the scan appliance surface data of the fourth digital 3D representation where they are arranged according to the arrangement of the patient's dental tissue relative to the scan appliance.

The transformation matrices may also be configured to provide that when applied to the scan appliance surface data of the fourth digital 3D representation these surface data are mapped into the same coordinate system as the dental tissue surface data of the second digital 3D representation where they are arranged according to the arrangement of the patient's dental tissue relative to the scan appliance.

When the opposing structure comprises teeth in the second one of the jaws, i.e. the first part of the scan appliance define the occlusion in collaboration with teeth in the second one of the jaws, the fourth digital 3D representation preferably comprises surface data relating to these teeth. In such cases it may be advantageous to determine the transformation matrices for aligning dental tissue surface data of the second and fourth digital 3D representations.

Accordingly, in some embodiments at least one of said transformation matrices is configured for aligning the dental tissue surface data of the second and fourth digital 3D representations.

The transformation matrix may be configured to provide that the dental tissue surface data of the second digital 3D representation are mapped into the coordinate system of the fourth digital 3D representation or that the scan appliance and dental tissue surface data of the fourth digital 3D representation are mapped into the coordinate system of the second digital 3D representation.

In both cases is provided that the scan appliance and dental tissue surface data of the fourth digital 3D representation and the dental tissue surface data of the second digital 3D representation are arranged according to the arrangement of the patient's dental tissue relative to the scan appliance.

The scan appliance may be digitally designed and manufactured using CAD/CAM techniques.

Disclosed is a method of producing a scan appliance, wherein the method comprises:

obtaining a digital 3D representation of a denture; and manufacturing the scan appliance from the digital 3D representation of a denture;

where one or more openings are defined in the scan appliance, said providing visual access to the dental tissue when the scan appliance is arranged at the patient's jaw.

This provides the advantage that the openings do not need to be made in the patient's existing denture, i.e. a denture already worn by the patient.

The digital 3D representation of the denture can be obtained by 3D scanning the existing denture using e.g. a desktop scanner and/or a handheld scanner, such as the scanner used for the intra-oral scanning.

In some embodiments, the one or more openings are defined by removing material from the body of the manufactured scan appliance, such as e.g. by drilling holes into the scan appliance body.

The scan appliance is thus manufactured from the digital 3D representation using e.g. direct digital manufacture techniques such as 3D printing or milling, and the openings are subsequently defined in the body of the scan appliance.

This provides the advantage that the scan appliance body can be manufactured at a remove facility, such as a dental lab, and the dentist who performs the scanning can determine where the openings are to be defined.

In some embodiments, the one or more openings are defined in the digital 3D representation of the denture. The openings can be defined in the digital 3D representation of the denture by a Boolean subtraction of e.g. a cylindrical CAD element.

The openings are thus defined prior to the manufacture of the scan appliance from the digital 3D representation and are thus already present in the scan appliance after the direct digital manufacture step.

This provides the advantage that no post processing, such as a removal of material from the body of the scan appliance, is required.

Disclosed is a method for determining the relative arrangement of a surface of a denture and a surface of the dental tissue of the jaw at which the denture is placed, the method comprising:

obtaining a first digital 3D representation comprising surface data relating to dental tissue in the jaw;

obtaining a third digital 3D representation comprising both surface data relating to the dental tissue in the jaw and surface data relating to the denture, where the denture comprises one or more openings through which the dental tissue surface data can be recorded from the first one of the jaws;

deriving one or more transformations for mapping the first and third digital 3D representations into the same coordinate system with a relative arrangement according to position of the denture at the jaw, where the one or more transformations at least partly are derived based on the dental tissue surface data recorded though the openings in the denture.

When the one or more transformations are determined based on the third digital 3D representation (which express the relative arrangement of the dental tissue surface and the denture surface) the relative arrangement of the denture surface and the dental tissue surface is determined.

In some embodiments, the surface of the denture is the occlusal surface of the denture teeth such that relative arrangement of the gum surface and the occlusal surface is determined. This information may be useful when e.g. designing an implant bar and corresponding denture for the patient.

Disclosed is a method for determining the relative arrangement of patient's jaws in a bite position when the patient's occlusion is not defined by natural teeth alone, the method comprising:

obtaining a first digital 3D representation comprising surface data relating to dental tissue in a first one of the patient's jaws;

obtaining a second digital 3D representation comprising surface data relating to dental tissue in a second one of the patient's jaws;

obtaining one or more further digital 3D representations, where:
  i. at least one of said further digital 3D representations comprises both surface data relating to the dental tissue in the first one of the patient's jaws and surface data relating to a first part of a scan appliance arranged in relation to the first one of the jaws, where the first part of the scan appliance is configured for at least partly defining the patient's occlusion in collaboration with an opposing structure at the second one of the jaws, and
  ii. at least one of the further digital 3D representations comprises surface data of the first part of the scan appliance and surface data relating to the opposing structure;

deriving one or more transformations for mapping the first and second digital 3D representations into the same coordinate system with a relative arrangement according to the relative arrangement of the jaws in the bite position, where at least one of the transformations at least partly is derived from surface data of the one or more further digital 3D representations.

In some embodiments, the one or more further digital 3D representations comprises a third digital 3D representation comprises the surface data relating to the dental tissue in the first one of the patient's jaws and the surface data relating to a first part of a scan appliance arranged in relation to the first one of the jaws and a fourth digital 3D representation comprising the surface data of the first part of the scan appliance and of the opposing structure. The third and fourth digital 3D representations may have been recorded in two separate 3D scans.

This may e.g. be the case when the first part of the scan appliance is a maxillary denture for the patient's upper jaw with openings at the patient's palette. If there is limited visual to the palette while the maxillary denture is arranged in occlusion with an opposing structure of the lower jaw and it may hence be advantageous that the third and fourth digital 3D representations are recorded in separate intra-oral 3D scans.

In some embodiments, the surface data relating to the dental tissue in the first one of the patient's jaws, the surface data relating to the first part of the scan appliance, and the surface data and of the opposing structure are contained in a single one of the further digital 3D representations.

This may e.g. be the case when the first part of the scan appliance is a maxillary denture for the patient's upper jaw with openings at the buccal surface allowing visual access to the alveolar ridge while still being able to define the patient's occlusion in collaboration with an opposing structure of the other jaw. It may also be the case when a single 3D scanning is used to record surface data both when the patient's bite is open such that e.g. openings at the palette can be accessed and when the patient's bite is closed, i.e. when the first part of the scan appliance is arranged in occlusion with the opposing structure.

In this case the relative arrangement of the dental tissue of the first one of the jaws and the opposing structure of the second one of the jaws can be derived directly from the single one of the further digital 3D representations.

Disclosed is a method for arranging digital 3D representations of a patient's jaws according to the arrangement of the jaws in a bite position when the patient's occlusion is not defined by natural teeth alone, the method comprising:

obtaining a first digital 3D representation comprising surface data relating to dental tissue in a first one of the patient's jaws;

obtaining a second digital 3D representation comprising surface data relating to dental tissue in a second one of the patient's jaws;

obtaining a third digital 3D representation comprising both surface data relating to the dental tissue in the first one of the patient's jaws and surface data relating to a first part of a scan appliance arranged in relation to the first one of the jaws, where the first part of the scan appliance is configured for at least partly defining the patient's occlusion in collaboration with an opposing structure at the second one of the jaws;

obtaining a fourth digital 3D representation comprising surface data of the first part of the scan appliance and surface data relating to the opposing structure; and arranging the first and second digital 3D representations in the same coordinate system according to the bite position of the jaws where the relative arrangement at least partly is based on surface data of the first and third digital 3D representations and/or on surface data of the third and fourth digital 3D representations.

In the context of the present invention the phrase "arranging the first and second digital 3D representations" both refer to the case where one or more transformations for bringing the first and second digital 3D representations into the same coordinate system with a relative arrangement according to the relative arrangement of the patient's jaws in the bite position are determined, and to the case where the arranging relates to expressing the two digital 3D representations in the same coordinate system with a relative arrangement according to the bite position defined by the scan appliance.

Disclosed is hence a method for determining the relative arrangement of a patient's jaws in a bite position when the patient's occlusion is not defined by natural teeth alone, the method comprising:
- obtaining a first digital 3D representation comprising surface data relating to dental tissue in a first one of the patient's jaws;
- obtaining a second digital 3D representation comprising surface data relating to dental tissue in a second one of the patient's jaws;
- obtaining a third digital 3D representation comprising both surface data relating to the dental tissue in the first one of the patient's jaws and surface data relating to a first part of a scan appliance arranged in relation to the first one of the jaws, where the first part of the scan appliance is configured for at least partly defining the patient's occlusion in collaboration with an opposing structure at the second one of the jaws;
- obtaining a fourth digital 3D representation comprising surface data of the first part of the scan appliance and surface data relating to the opposing structure; and
- mapping or determining transformation matrices for mapping the first and second digital 3D representations into the same coordinate system at least partly based on surface data of the third and fourth digital 3D representations.

Disclosed is a method for determining the relative arrangement of patient's jaws in a bite position when the patient's occlusion at least partly is defined by a first denture, the method comprising:
- obtaining a first digital 3D representation comprising surface data relating to dental tissue in a first one of the patient's jaws;
- obtaining a second digital 3D representation comprising surface data relating to dental tissue in a second one of the patient's jaws;
- obtaining a first denture digital 3D representation by 3D scanning a first denture comprising a first set of denture teeth and a first denture base, where the first denture base comprises a gum-facing surface configured for engaging the gum of the first one of the patient's jaws, and where the first denture digital 3D representation comprises surface data for the first set of denture teeth and surface data for the gum-facing surface of the first denture base;
- obtaining a fourth digital 3D representation which has been recorded with the first denture arranged in relation to the first one of the patient's jaws and in occlusion with an opposing structure at the second one of the patient's jaws such that the fourth digital 3D representation comprises surface data of the first denture and surface data relating to the opposing structure; and
- mapping or determining one or more transformations for mapping the first and second digital 3D representations into the same coordinate system at least partly based on surface data of the first denture digital 3D representation and the fourth digital 3D representation.

The surface data of the first denture digital 3D representation and the fourth digital 3D representation can be used to determine the relative arrangement of the gum facing surface of the first denture and the opposing structure of the second one of the jaws.

In some embodiments, the mapping comprises aligning the dental tissue surface data of the first digital 3D representations with the surface data for the gum-facing portion of the base of the first denture provided in the first denture digital 3D representation. A transformation configured for such an alignment provides that the surface data of the first digital 3D representation describing the shape of the dental tissue of the first one of the jaws is linked to the surface of the first denture and in particular to the teeth of the first denture. The relative arrangement of the denture (i.e. denture teeth and gum facing surface of the denture base) and the gum surface of the first one of the jaws is hence determined. This transformation may be derived from an ICP algorithm aligning the dental tissue surface data of the first digital 3D representation with the surface data for the gum facing surface of the first denture digital 3D representation.

In some embodiments, the method comprises deriving a transformation for arranging the denture teeth surface data of the first denture digital 3D representation and the corresponding surface data of the fourth digital 3D representation relative to each other. This provides that the relative arrangement of the first denture and the opposing structure in the second one of the jaws in the bite position is determined. This transformation may be derived from an ICP algorithm aligning the denture teeth surface data of the first denture digital 3D representation with the corresponding surface data of the fourth denture digital 3D representation When the transformation for arranging the first digital 3D representation relative to the first denture digital 3D representation and the transformation for arranging the first denture digital 3D representation relative to the fourth digital 3D representation are determined, the correct relative arrangement of the dental tissue of the first jaw (comprised in the first digital 3D representation) and of the surface data for the opposition structure (comprised in the fourth digital 3D representation) is known.

In some cases the patient has teeth in the second one of the jaws forming at least part of the opposing structure such that the first denture at the first jaw and the teeth in the second jaw together define the patient's occlusion. The surface data of the fourth digital 3D representation relating to the opposing structure may then comprise surface data for the teeth of the second on of the jaws. In such cases the method may comprise deriving a transformation for arranging the dental tissue surface data of the second digital 3D representation and the surface data of the fourth digital 3D representation relative to each other, where the dental tissue surface data comprises surface data relating to the teeth in the second jaw. This transformation may be derived from an ICP algorithm aligning the dental tissue surface data of the second and fourth digital 3D representations.

The relative arrangement of the gum facing surface of the first denture and the teeth of the second one of the jaws in the bite position can be determined via the transformation which arranges the surface data of the first denture digital 3D representation and the fourth digital 3D representation relative to each other.

When transformation for mapping the first and the fourth digital 3D representations into the same coordinate system and for mapping the second and fourth digital 3D representation into the same coordinate system, the relative arrangement of the jaws has been determined.

In some cases the patient has a denture at both jaws, where the first denture at the first jaw and the second denture at the second jaw together define the patient's occlusion.

In some embodiments the method comprises:
- obtaining a second denture comprising a second set of denture teeth and a second denture base, where the second denture base comprises a gum-facing surface configured for engaging the gum of a second one of the patient's jaws, and obtaining a second denture digital 3D representation by 3D scanning the second denture, where the second denture digital 3D representation comprises surface data for the second set of denture teeth and surface data for the gum-facing surface of the second denture base; where mapping the first and second digital 3D representations into the same coordinate system at least partly based on surface data of the second denture digital 3D representation and the fourth digital 3D representation.

The surface data of the second denture digital 3D representation and the fourth digital 3D representation can be used to determine the relative arrangement of the gum facing surface of the second denture and the first denture in the bite position. Since the position of the dental tissue of the first one of the jaws is linked to the surface of the first denture this information can be used when determining the relative arrangement of the jaws in the bite position.

In some embodiments, the method comprises deriving a transformation for mapping the dental tissue surface data of the second digital 3D representations with the surface data for the gum-facing portion of the base of the second denture provided in the second denture digital 3D representation. A transformation configured for such an alignment provides that the surface data of the second digital 3D representation describing the shape of the dental tissue of the second one of the jaws is linked to the surface of the second denture. Then the relative arrangement of the second denture (i.e. denture teeth and gum facing surface of the denture base) and the gum surface of the second one of the jaws is hence determined.

When transformations for linking the first and second digital 3D representations via a first denture digital 3D representation (and optionally a second denture digital 3D representation) have been determined, the relative arrangement of the first and second one of the jaws in the bite position has been determined, Disclosed is a method for determining the relative arrangement of patient's jaws in a bite position when the patient's occlusion is not defined by natural teeth alone, the method comprising:
  obtaining a first and a second digital 3D representation comprising surface data relating to dental tissue in a first and second one of the patient's jaws, respectively;
  arranging a first part of a scan appliance in the patient's mouth where the first part of the scan appliance is configured for at least partly defining the patient's occlusion in collaboration with an opposing structure at the second one of the jaws and the first part comprises one or more openings providing visual access to parts of the patients dental tissue otherwise covered by the scan appliance;
  obtaining a third digital 3D representation comprising both surface data relating to the dental tissue in the first one of the patient's jaws and surface data relating to the first part of a scan appliance;
  obtaining a fourth digital 3D representation comprising surface data of the first part of the scan appliance and surface data relating to the opposing structure; and
  determining the relative arrangement of the patient's first and second jaws in occlusion, where the determining comprises mapping the first and second digital 3D representations into the same coordinate system.

In some embodiments, mapping the first and second digital 3D representations into the same coordinate system is at least partly based on surface data of the third and fourth digital 3D representations.

Disclosed is a method of generating a data file comprising surface data of dental tissue in a patient's jaws and information expressing the relative arrangement of the jaws a bite position when the patient's occlusion is not defined by natural teeth alone, the method comprising:
  obtaining a first digital 3D representation comprising surface data relating to dental tissue in a first one of the patient's jaws;
  obtaining a second digital 3D representation comprising surface data relating to dental tissue in a second one of the patient's jaws;
  obtaining a third digital 3D representation comprising both surface data relating to the dental tissue in the first one of the patient's jaws and surface data relating to a first part of a scan appliance arranged in relation to the first one of the jaws, where the first part of the scan appliance is configured for at least partly defining the patient's occlusion in collaboration with an opposing structure at the second one of the jaws;
  obtaining a fourth digital 3D representation comprising surface data of the first part of the scan appliance and surface data relating to the opposing structure; and
  generating said data file, where the generating comprises deriving one or more transformations for mapping the first and second digital 3D representations into the same coordinate system.

In some embodiments, the one or more transformations for mapping the first and second digital 3D representations into the same coordinate system are at least partly derived from surface data of the third and fourth digital 3D representations.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

Disclosed is a non-transitory computer readable medium storing thereon a computer program, where said computer program is configured for causing computer-assisted determining of the relative arrangement of patient's jaws in a bite position when the patient's occlusion is not defined by natural teeth alone, where the computer program is configured for deriving one or transformations for mapping a first and a second digital 3D representation into the same coordinate system, wherein
  the first and second digital 3D representation comprises surface data relating to dental tissue in a first and second one of the patient's jaws, respectively;
  a third digital 3D representation comprises both surface data relating to the dental tissue in the first one of the patient's jaws and surface data relating to a first part of a scan appliance arranged in relation to the first one of the jaws while the third digital 3D representation is recorded, where the first part of the scan appliance is configured for at least partly defining the patient's occlusion in collaboration with an opposing structure at the second one of the jaws; and
  a fourth digital 3D representation comprises surface data of the first part of the scan appliance and surface data relating to the opposing structure.

Disclosed is system for determining of the relative arrangement of patient's jaws in a bite position when the patient's occlusion is not defined by natural teeth alone, where the computer program is configured for mapping a first and a second digital 3D representation into the same coordinate system at least partly based on surface data of a third and fourth digital 3D representations, wherein the system comprises a non-transitory computer readable medium having one or more computer instructions stored thereon, where said computer instructions comprises instructions for deriving one or more transformations for mapping a first and a second digital 3D representation into the same coordinate system at least partly based on surface data of a third and fourth digital 3D representations, wherein the first and second digital 3D representation comprises surface data relating to dental tissue in a first and second one of the patient's jaws, respectively;

the third digital 3D representation comprises both surface data relating to the dental tissue in the first one of the patient's jaws and surface data relating to a first part of a scan appliance arranged in relation to the first one of the jaws, where the first part of the scan appliance is configured for at least partly defining the patient's occlusion in collaboration with an opposing structure at the second one of the jaws; and the fourth digital 3D representation comprises surface data of the first part of the scan appliance and surface data relating to the opposing structure.

The present invention relates to different aspects including the method and system described above and in the following, and corresponding methods and systems, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 1A and 1B illustrate possible workflows.

DETAILED DESCRIPTION

In the following description, reference is made to the accompanying figures, which show by way of illustration how the invention may be practiced.

FIG. 1A shows the workflow an embodiment of the method for determining the relative arrangement of patient's jaws in a bite position when the patient's occlusion is not defined by natural teeth alone.

In step 101 a first digital 3D representation comprising surface data relating to dental tissue in a first one of the patient's jaws is obtained.

In step 102 a second digital 3D representation comprising surface data relating to dental tissue in a second one of the patient's jaws is obtained.

When the relative arrangement of the jaws is determined with the purpose of designing dentures for the patient's jaws, the first and second digital 3D representations preferably express the shape of the dental tissue in the first and second jaws to such an extent that the base part of the dentures for the first and second jaws can be designed based on the first and second digital 3D representations.

In step 103 a first part of a scan appliance is arranged in relation to the first one of the jaws, where the first part of the scan appliance is configured for at least partly defining the patient's occlusion in collaboration with an opposing structure at the second one of the jaws.

In step 104 a third digital 3D representation comprising both surface data relating to the dental tissue in the first one of the patient's jaws and surface data relating to the first part of the scan appliance is obtained while the first part of the scan appliance is arranged at the first one of the patient's jaws. The third digital 3D representation thus provides information of the spatial relationship between the dental tissue in the first jaw and the surface of the first part of the scan appliance.

In step 105 a fourth digital 3D representation comprising surface data of the first part of the scan appliance and surface data relating to the opposing structure is obtained.

This digital 3D representation is analog to a so-called "bite scan" since it holds information about the relative arrangement of the jaws in the bite position. Here the bite is defined at least partly by the scan appliance.

In step 106 the first and second digital 3D representations are mapped into the same coordinate system and/or one or more transformations for this mapping are derived.

Figure 1B:
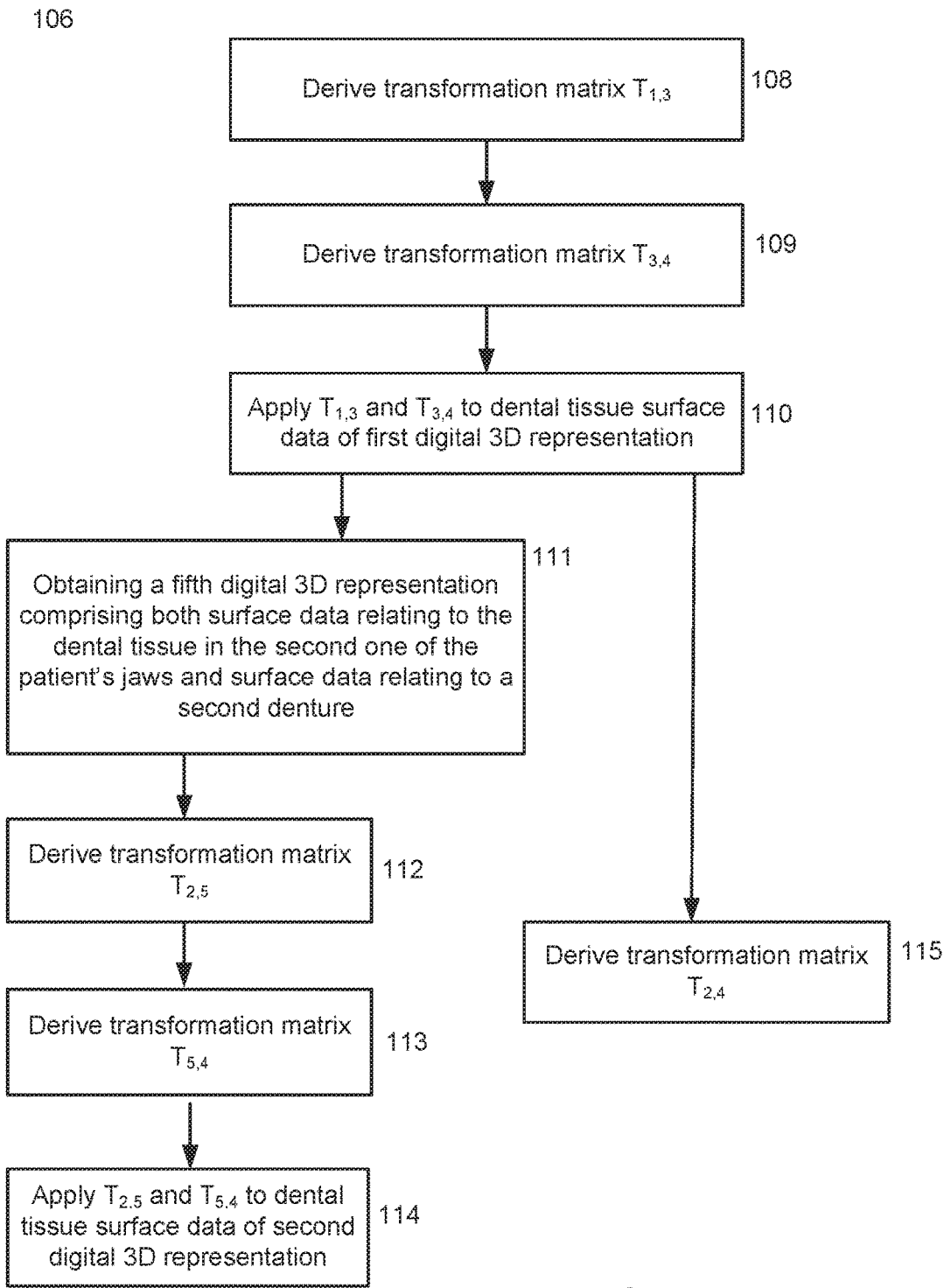

FIG. 1B shows a workflow for determining transformations for mapping the first and second digital 3D representations into the coordinate system of the fourth digital 3D representation.

When the derived transformations are applied to the first and second digital 3D representations these will be arranged according to the relative arrangement of the first and second jaws in the bite position. In this example the transformations are all expressed in terms of transformation matrices.

In step 108 a transformation matrix ($T_{1,3}$) for transforming the first digital 3D representation such that its dental tissue surface data are aligned with the corresponding surface data of the third digital 3D representations is derived. I.e. the transformation matrix $T_{1,3}$ is derived based on surface data of the first and third digital 3D representations relating to the same dental tissue of the first one of the jaws.

The transformation matrices can be determined using e.g. a computer implemented Iterative Closest Point (ICP) algorithm.

In step 109 a transformation matrix ($T_{3,4}$) for transforming the third digital 3D representation such that its scan appliance surface data are aligned with the corresponding surface data of the fourth digital 3D representations is derived. I.e. the transformation matrix $T_{3,4}$ is derived based on surface data of the third and fourth digital 3D representations relating to the first part of the scan appliance.

In step 110 the first digital 3D representation is mapped into the coordinate system of the fourth digital 3D representation by applying the transformation matrices ($T_{1,3}$) and ($T_{3,4}$) to the surface data of the first digital 3D representation.

Applying the transformation matrices $T_{1,3}$ and $T_{3,4}$ to the dental tissue surface data of the first digital 3D representation in step 110 provides that the first digital 3D representation is transformed such that its dental tissue surface data are arranged correctly relative to the fourth digital 3D representation.

In some cases, e.g. for a completely edentulous patient having no natural teeth in either of his jaws, a second part of the scan appliance can be arranged in relation to the second one of the patient's second jaws where it can collaborate with the first part of the scan appliance in defining the occlusion.

The first and second parts of the scan appliance can be a first and a second denture where the denture teeth engage each other in the patient's bite position and define the occlusion.

The second denture is arranged in relation to the second one of the jaws and in step 111 a fifth digital 3D representation comprising both surface data relating to the dental tissue in the second one of the patient's jaws and surface data relating to the second denture is obtained.

The second and fifth digital 3D representations both comprise surface data relating to the same dental tissue of the second one of the jaws. A transformation arranging the second digital 3D representation relative to the fifth digital 3D representation can hence be derived by aligning the dental tissue surface data of these two digital 3D representations. This can be done using e.g. a computer implemented Iterative Closest Point (ICP) algorithm to the second digital 3D representation keeping the fifth digital 3D representation fixed.

The fifth and fourth digital 3D representations both comprise surface data relating to the second part of the scan appliance allowing a transformation for arranging these two digital 3D representations to be derived by aligning the scan appliance surface data using an ICP algorithm.

In step 112 a transformation matrix ($T_{2,5}$) for transforming the second digital 3D representation such that its dental tissue surface data are aligned with the corresponding surface data of fifth digital 3D representations is derived. The transformation matrix $T_{2,5}$ is hence derived based on surface data of the second and fifth digital 3D representations relating to the same dental tissue of the second one of the jaws.

In step 113 a transformation matrix ($T_{5,4}$) for transforming the fifth digital 3D representation such that its scan appliance surface data are aligned with the corresponding surface data of the fourth digital 3D representations is derived. The transformation matrix $T_{5,4}$ is derived based on surface data of the fifth and fourth digital 3D representations relating to the second part of the scan appliance.

In step 114 the $T_{2,5}$ and $T_{5,4}$ transformation matrices are applied to the surface data of the second digital 3D representation. Applying the transformation matrices $T_{2,5}$ and $T_{5,4}$ to the dental tissue surface data of the second digital 3D representation provides that the second digital 3D representation is transformed such that its dental tissue surface data are arranged correctly relative to the fourth digital 3D representation.

The dental tissue surface data of the second digital 3D representation are then mapped into the coordinate system of the fourth digital 3D representation via the fifth digital 3D representation comprising surface data relating both to the dental tissue in the second one of the jaws and to the second part of the scan appliance.

If the patient has sufficient teeth in the second jaw to provide that the first part of the scan appliance can define the occlusion in collaboration with these teeth it may be unnecessary to the use a second part of the scan appliance. Instead the second digital 3D representation comprises dental tissue surface data relating to these teeth such that a transformation matrix ($T_{2,4}$) for aligning the second and fourth digital 3D representations can be determined 115. Applying this transformation matrix to the dental tissue surface data of the second digital 3D representation provides that these surface data are expressed in the coordinate system of the fourth digital 3D representation.

In both cases the results of a process involving steps 108-114 or a process involving steps 108-110 and 115 is that the first and second digital 3D representations are mapped into the coordinate system of the fourth digital 3D representation whereby the dental tissue surface data of the first and second digital 3D representations are expressed in the same coordinate system according to the relative arrangement of the dental tissue of the jaws in the bite position defined at least partly by the scan appliance. The relative arrangement of the jaws in the bite position is thereby determined.

The digital 3D representations can be obtained by intra-oral scanning where an intra-oral scanner, e.g. the TRIOS scanner by 3 shape A/S, is used for recording the geometry and optionally also the color of the dental tissue and scan appliance.

The intra-oral scanner may be configured for utilizing focus scanning, where the digital 3D representation of the scanned dental tissue or scan appliance is reconstructed from in-focus images acquired at different focus depths. The focus scanning technique can be performed by generating a probe light and transmitting this probe light towards the dental tissue such that at least a part of the dental tissue is illuminated. Light returning from e.g. the dental tissue is transmitted towards a camera and imaged onto an image sensor in the camera by means of an optical system, where the image sensor/camera comprises an array of sensor elements. The position of the focus plane on/relative to the dental tissue is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the dental tissue and optionally a scan appliance arranged at the jaw can be derived.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

Figure 2A:
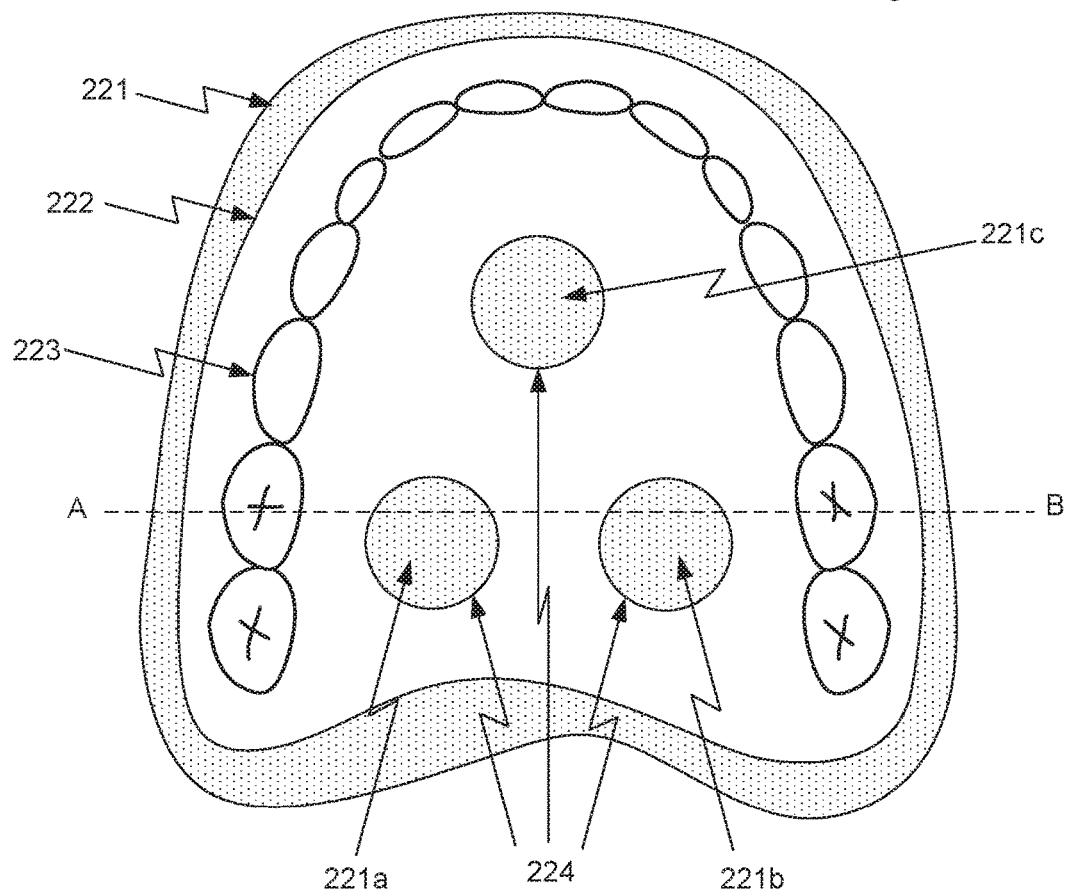
FIGS. 2A and 2B show a schematic of a part of a scan appliance based on a maxillary denture.
Figure 2B:
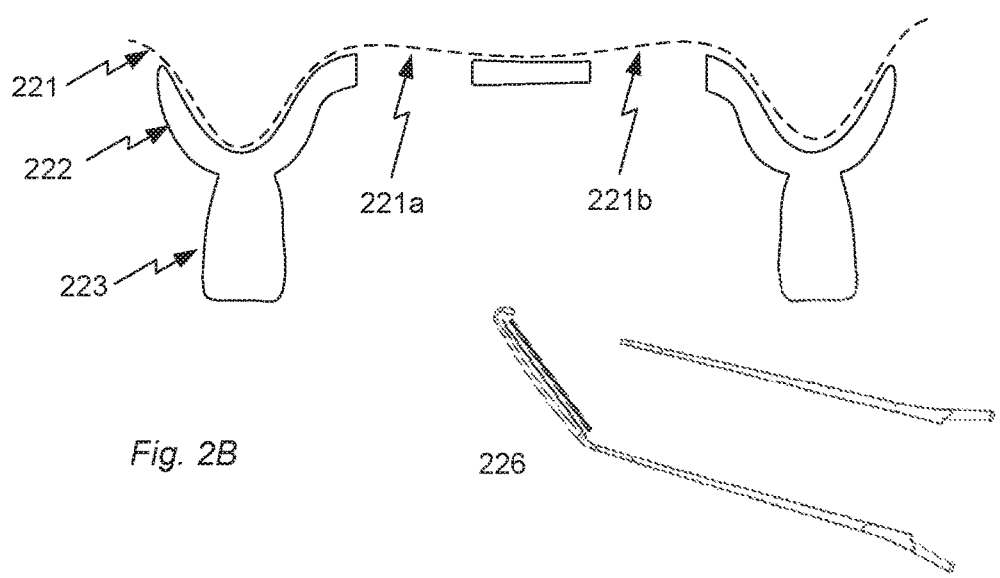

FIGS. 2A and 2B show a schematic of a scan appliance part based on a maxillary denture. The denture teeth 223 are secured in the denture base 222 which contacts the patient's gums in the patient's mouth. The illustrated denture is for a completely edentulous upper jaw and the denture teeth 223 define the occlusion in collaboration with an opposing structure in the lower jaw.

In FIG. 2A the dental tissue 221, 221a, 221b, 221c and the maxillary denture 222, 223 is viewed from the occlusal plane. Three openings 224 have been defined by drilling holes through the denture base 222 such that visual access is provided to the dental tissue 221a, 221b, 221c otherwise covered by the denture. Arranging holes in the denture to provide visual access to the patient's palette is advantageous since this often forms a structure which is good for aligning surface data of different digital 3D representations, such as surface tissue data for the palette in the first and third digital 3D representations.

FIG. 2B shows a cross section of the denture/dental tissue at the dotted line A-B as seen from a direction perpendicular to the occlusal plane. Here it is illustrated that the denture base 222 covers the dental tissue 221 except at the boundary of the denture and at the openings defined in the denture base where surface data relating to dental tissue 221a, 221b can be recorded using an intra-oral scanner 226. A 3D scanning can then provide a third digital 3D representation comprising both surface data relating to the dental tissue 221a, 221b and surface data relating to the denture base 222 and teeth 223, where the third digital 3D representation expresses the relative arrangement of these surfaces.

Figure 3A:
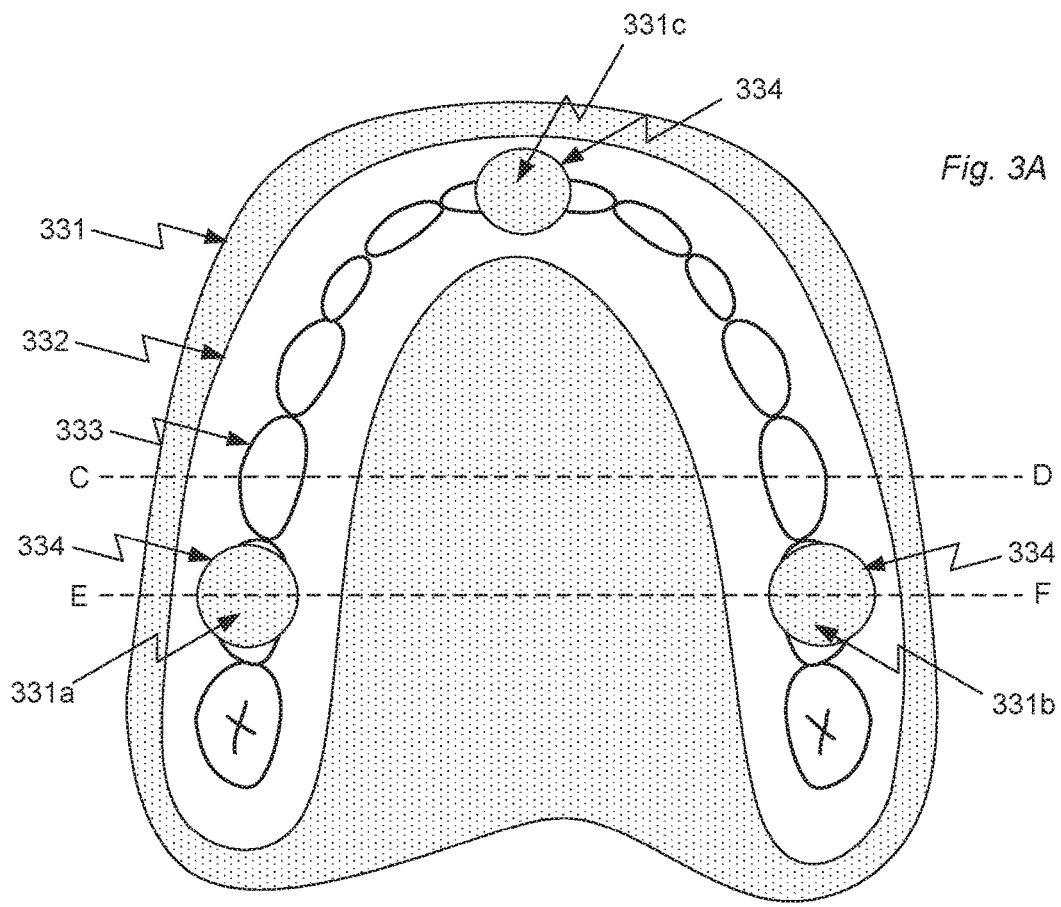
FIGS. 3A-3C show a schematic of a part of a scan appliance based on a mandibular denture.
Figure 3B:
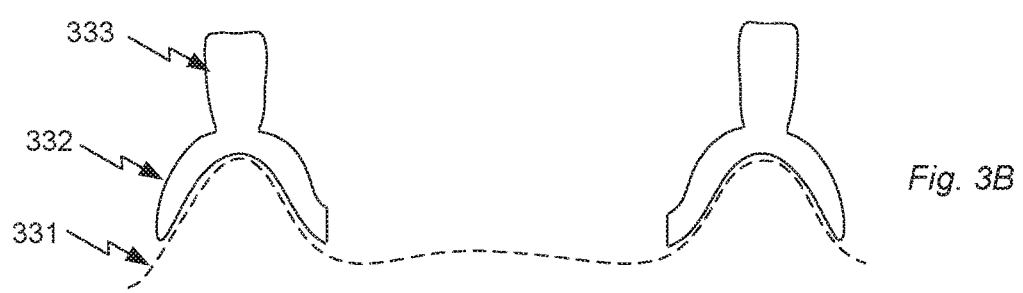
Figure 3C:
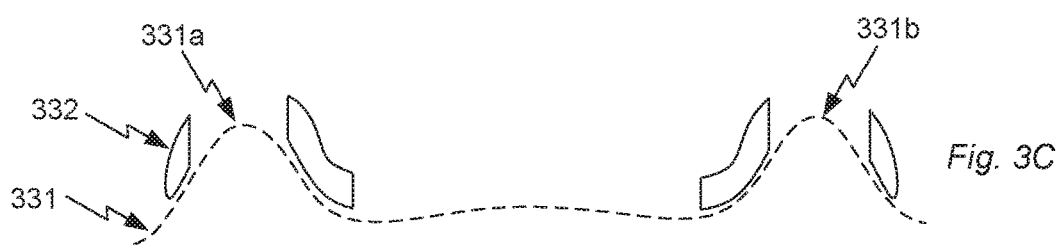

FIGS. 3A-3C show a schematic of a scan appliance based on a mandibular denture. The denture teeth 333 are secured in the denture base 332 which contacts the dental tissue of the patient's gums 331. The illustrated denture is for a completely edentulous upper jaw and the denture teeth 333 define the occlusion in collaboration with an opposing structure in the upper jaw, such as e.g. the maxillary denture illustrated in FIGS. 2A and 2B.

In FIG. 3A the dental tissue 331, 331a, 331b, 331c and the mandibular denture 332, 333 is viewed from the occlusal plane. Three openings 334 have been defined by drilling holes through the denture teeth 333 and denture base 332 such that visual access is provided to the dental tissue 331a, 331b, 331c otherwise covered by the denture.

FIG. 3B shows a cross section of the denture/dental tissue at the dotted line C-D as seen from a direction perpendicular to the occlusal plane. The mandibular denture is shaped to follow the patient's arch and hence has an open area where gums are visible. However the gum tissue below this open area does not provide structure which allows for an alignment of digital 3D representations and further the tongue will at least partly obstruct the path for an intra-oral scanner in this region. The dental/gum tissue 331 at the alveolar ridge could be used for alignment but this is covered by the denture 332, 333.

FIG. 3C shows a cross section of the denture/dental tissue at the dotted line E-F as seen from a direction perpendicular to the occlusal plane. This line intersects the openings defined in the denture and as can be seen in FIG. 3C the openings provide visual access to dental tissue 331a, 331b at the alveolar ridge. A 3D scanning using an intra-oral scanner can then provide a fifth digital 3D representation comprising both surface data relating to the dental tissue 331a, 331b and surface data relating to the denture 332, 333 where the fifth digital 3D representation expresses the relative arrangement of these surfaces.

FIGS. 4 and 5 illustrate a case where both the upper and lower jaws are completely edentulous and the occlusion is defined by a scan appliance which consists of existing dentures for the upper and lower jaws, i.e. a maxillary and a mandibular denture, or copies of the dentures where openings are defined in each denture e.g. by drilling away denture material. In the following the first and second one of the jaws are the upper and lower jaws, respectfully, without limiting the scope of the application and claims to this combination. Further the order of the steps is not limited by the order described here. In the illustrated case the first and second digital 3D representations are both mapped into the coordinate system of the fourth digital 3D representation. For the first digital 3D representation the mapping is based on the third and fourth digital 3D representations, while the mapping of the second digital 3D representation is based on the fifth and fourth digital 3D representations.

The schematic drawings of FIGS. 4 and 5 illustrate the cross sectional views of the dental tissue, scan appliance parts and digital 3D representations corresponding to those used in FIGS. 2B, 3B and 3C.

FIGS. 4A-4H illustrate the digital 3D representations recorded during one embodiment and how the denture based scan appliance parts are arranged in the mouth while recording some of these digital 3D representations.

Figure 4A:
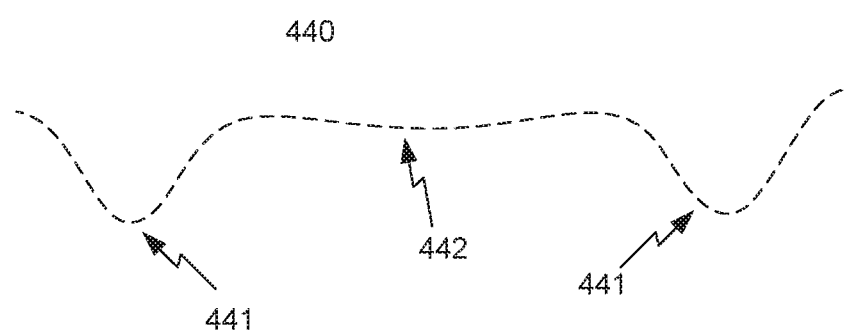
FIGS. 4A-4H illustrate the digital 3D representations recorded during one embodiment.

FIG. 4A shows a cross section of a first digital 3D representation comprising surface data 440 relating to dental tissue in the upper jaw. The cross section corresponds to the line A-B seen in FIG. 2A. This digital 3D representation is recorded by e.g. intra-oral scanning with the first part of the scan appliance removed from the patient's mouth such that surface data relating to the alveolar ridge 441 of the upper jaw and preferably to the palette 442 are comprised in the first digital 3D representation.

Figure 4B:
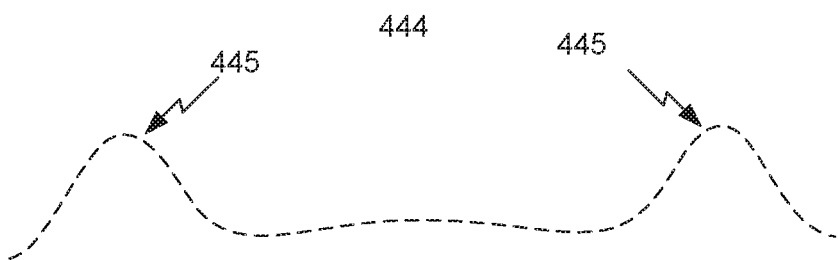

FIG. 4B shows a cross section of a second digital 3D representation comprising surface data 444 relating to dental tissue in the lower jaw. The cross section corresponds to the line E-F seen in FIG. 3A. This digital 3D representation is recorded by e.g. intra-oral scanning with the second part of the scan appliance removed from the patient's mouth such that surface data relating to the alveolar ridge 445 of the lower jaw are comprised in the second digital 3D representation.

The first and second digital 3D representations can also be obtained by obtaining a physical impression of the corresponding jaw and either scanning the impression or a physical model of the jaw manufactured from the impression.

Figure 4C:
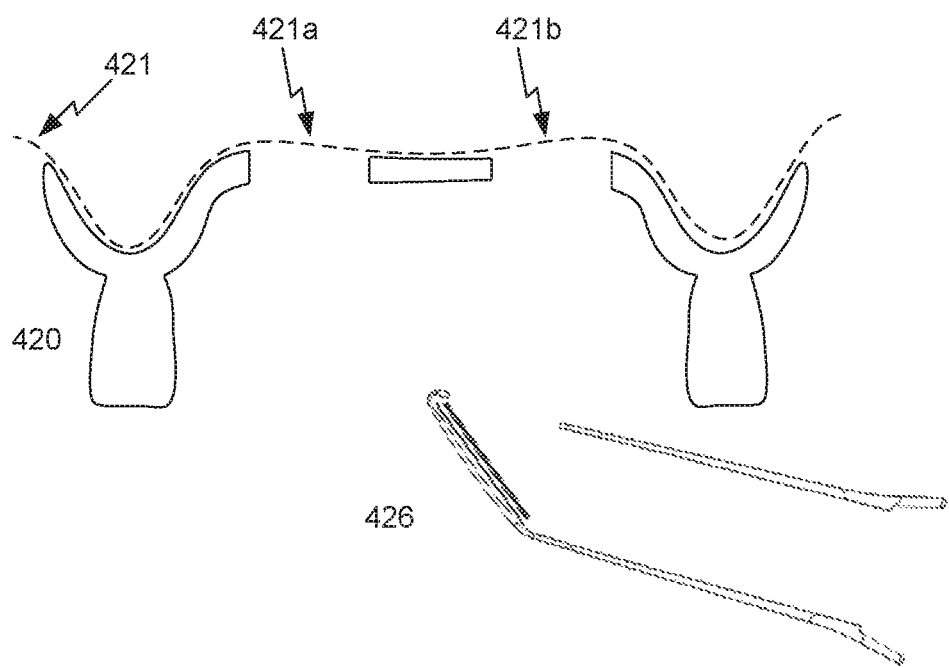

FIG. 4C illustrates the arrangement of the first part of the scan appliance 420 in relation to the dental tissue of the patient's upper jaw 421. The openings made in the maxillary denture provide visual access to the dental tissue 421a, 421b below such that the intra-oral scanner 426 can record a third digital 3D representation comprising surface data relating to the scan appliance in the upper jaw and surface data relating to the visible dental tissue 421a, 421b as explained in relation to FIG. 2B.

Figure 4D:
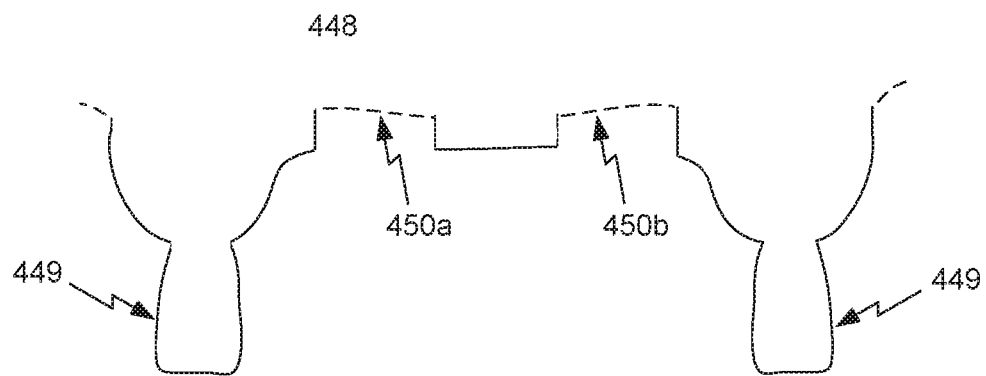

FIG. 4D shows a cross section of the third digital 3D representation obtained by intra-oral scanning with the first part of the scan appliance at the upper jaw. The cross section corresponds to the line A-B seen in FIG. 2A. The surface data 448 of the third digital 3D representation comprises surface data relating to the first part of the scan appliance 449 and surface data relating to the dental tissue 450a, 450b visible through the openings in the scan appliance.

Figure 4E:
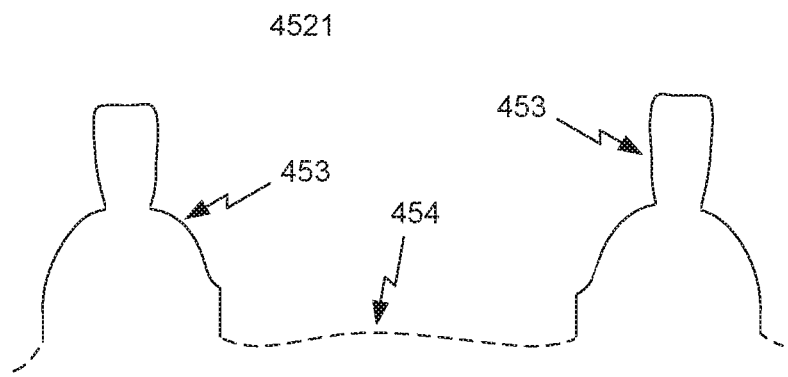
Figure 4F:
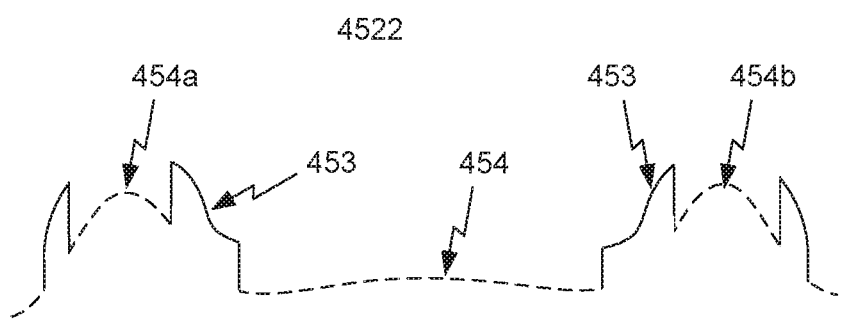

FIGS. 4E and 4F show cross sections 4521, 4522 of surface data of a fifth digital 3D representation obtained by intra-oral scanning with the second part of the scan appliance at the lower jaw as illustrated in FIGS. 3A-3C. The cross sections 4521, 4522 correspond to the lines C-D and E-F of FIG. 3A, respectively. The fifth digital 3D representation comprises surface data 453 relating to the second part of the scan appliance (full line) and surface data 454, 454a, 454b relating to the dental tissue of the lower jaw (dotted line). A transformation matrix for transforming e.g. the second digital 3D representation to be arranged correctly relative to the fifth digital 3D representation can be derived based on the dental tissue surface data 454a, 454b recorded through the openings of the mandibular denture rather than the surface data 454 for the dental tissue below the tongue.

Figure 4G:
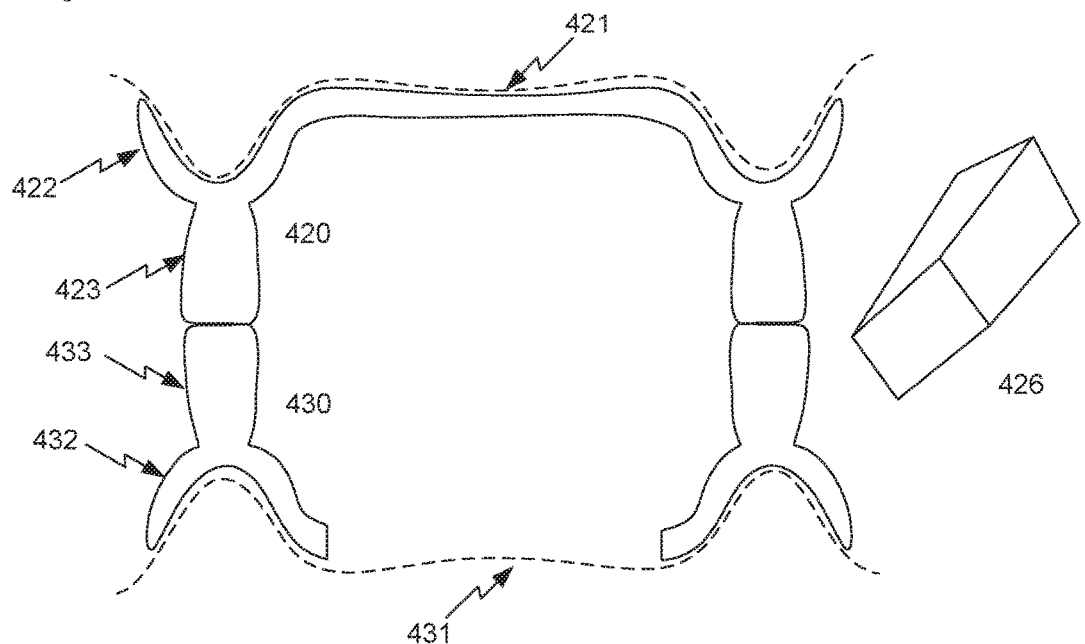

FIG. 4G illustrates the arrangement of the first 420 and second 430 parts of the scan appliance in relation to the dental tissue of the patient's upper jaw 421 and lower jaw 431. The patient's jaws are held in a bite position where the teeth 423 of the maxillary denture (the first part of the scan appliance) engage the teeth 433 of the mandibular denture (the second part of the scan appliance) while the base parts 422, 432 engages the dental tissue in the upper and lower jaws. The intra-oral scanner 426 can then record a bite scan which provides information of the relative arrangement of the scan appliance parts (i.e. the dentures) in the bite position.

Figure 4H:
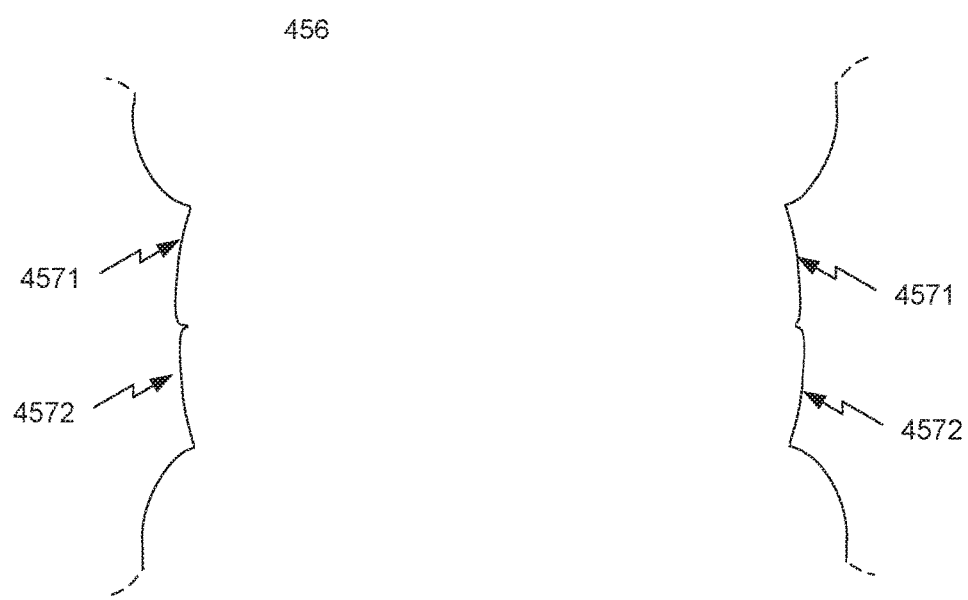

FIG. 4H shows a cross section of surface data 456 of a fourth digital 3D representation obtained by intra-oral scanning of the bite with the scan appliance parts arranged as illustrated in FIG. 4G. The fourth digital 3D representation comprises surface data 4571 relating to the first part and surface data 4572 relating to the second part of the scan appliance. The cross section corresponds to the line A-B seen in FIG. 2A.

FIGS. 5A-5H illustrate the effect of transformation matrices for mapping digital 3D representations of the dental tissue in the patient's upper and lower jaws into the coordinate system of a bite scan. The cross sections seen in this figure corresponds to the line A-B seen in FIG. 2A.

Figure 5A:
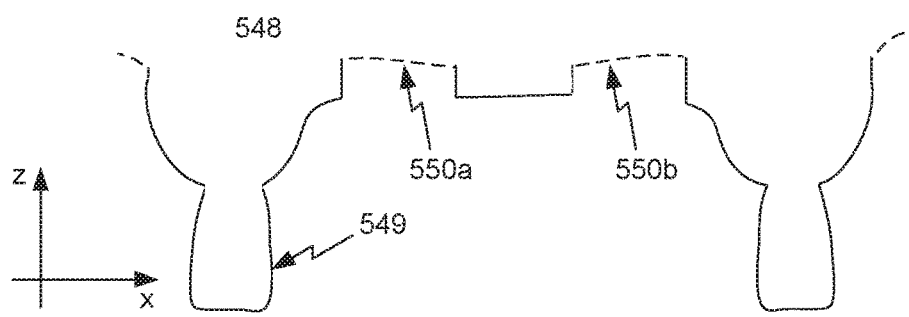
FIGS. 5A-5H illustrate mapping into a coordinate system of a bite scan.

FIG. 5A shows the same cross section of the third digital 3D representation as seen in FIG. 4D. The third digital 3D representation comprises dental tissue surface data 550a, 550b for the upper jaw and surface data 549 relating to the first part of the scan appliance.

Figure 5B:
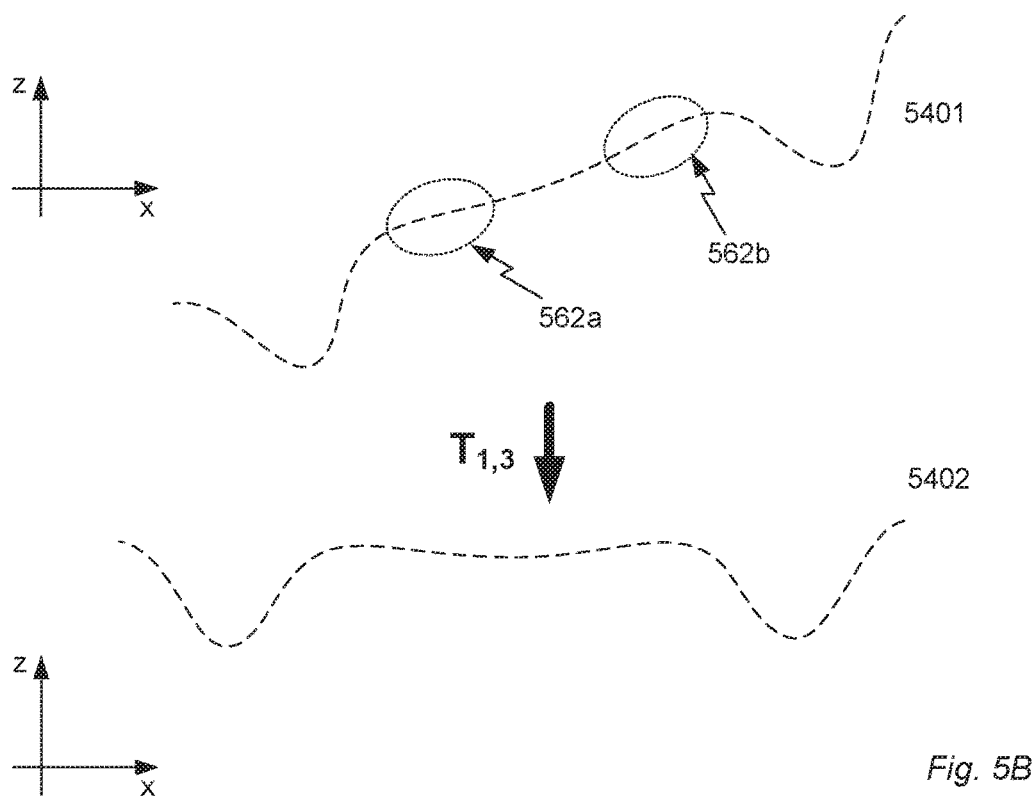

FIG. 5B illustrates the effect of applying a first transformation matrix $T_{1,3}$ on the first digital 3D representation comprising dental tissue surface data 5401 of the upper jaw. The transformation provides that the transformed first digital 3D representation is displaced and rotated by 20 degrees (relative to the third digital 3D representation).

The surface data 550a, 550b of the third digital 3D representation 548 and the surface data of the first digital 3D representation 5401 enclosed by the circles 562a, 562b relate to the same dental tissue of the upper jaw. The first transformation matrix $T_{1,3}$ is derived by aligning the surface data of the first and third 3D representations relating to the matching enclosed portions of the dental tissue using e.g. computer implemented Iterative Closest Point algorithms. The effect of applying the first transformation matrix $T_{1,3}$ on all dental tissue surface data 5401 of the first digital 3D representation is that the dental tissue surface data 5402 of the transformed first digital 3D representation are mapped into the coordinate system of the third digital 3D representation, i.e. the transformation matrix $T_{1,3}$ compensates for the displacement and the 20 degree rotation.

Figure 5C:
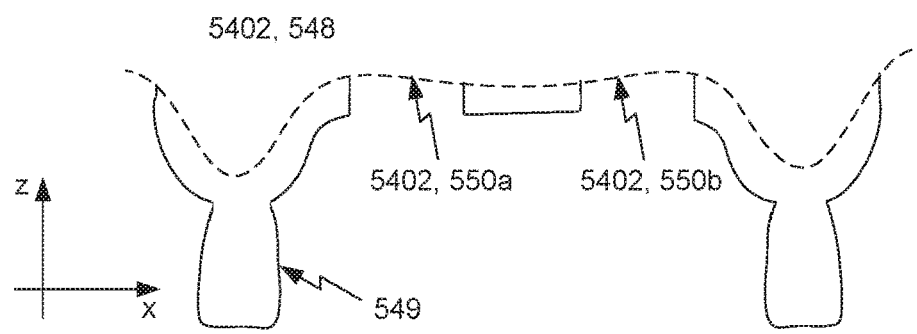

After such a transformation the dental tissue surface data 5402 of the transformed first digital 3D representation and the surface data 548 of the third digital 3D representation relating to the first part of the scan appliance are arranged in the same coordinate system according to the relative arrangement of the first part of the scan appliance and the dental tissue of the upper jaw. This is illustrated in FIG. 5C.

Figure 5D:
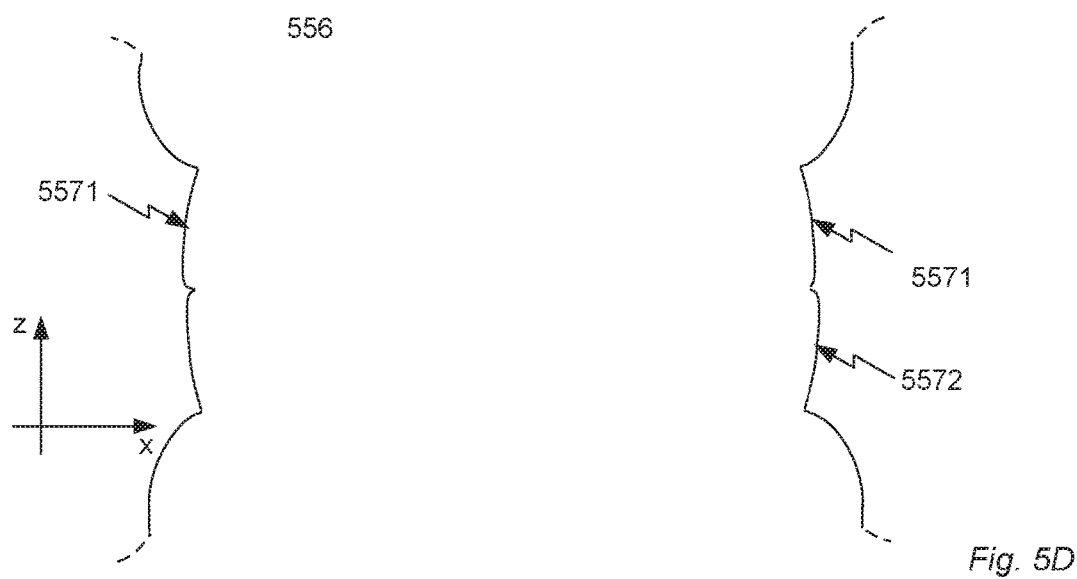

FIG. 5D shows the same cross section of the fourth digital 3D representation as seen in FIG. 4H. The fourth digital 3D representation 556 comprises scan appliance surface data 5571, 5572 relating to buccal surfaces of the first and second parts of the scan appliance.

Figure 5E:
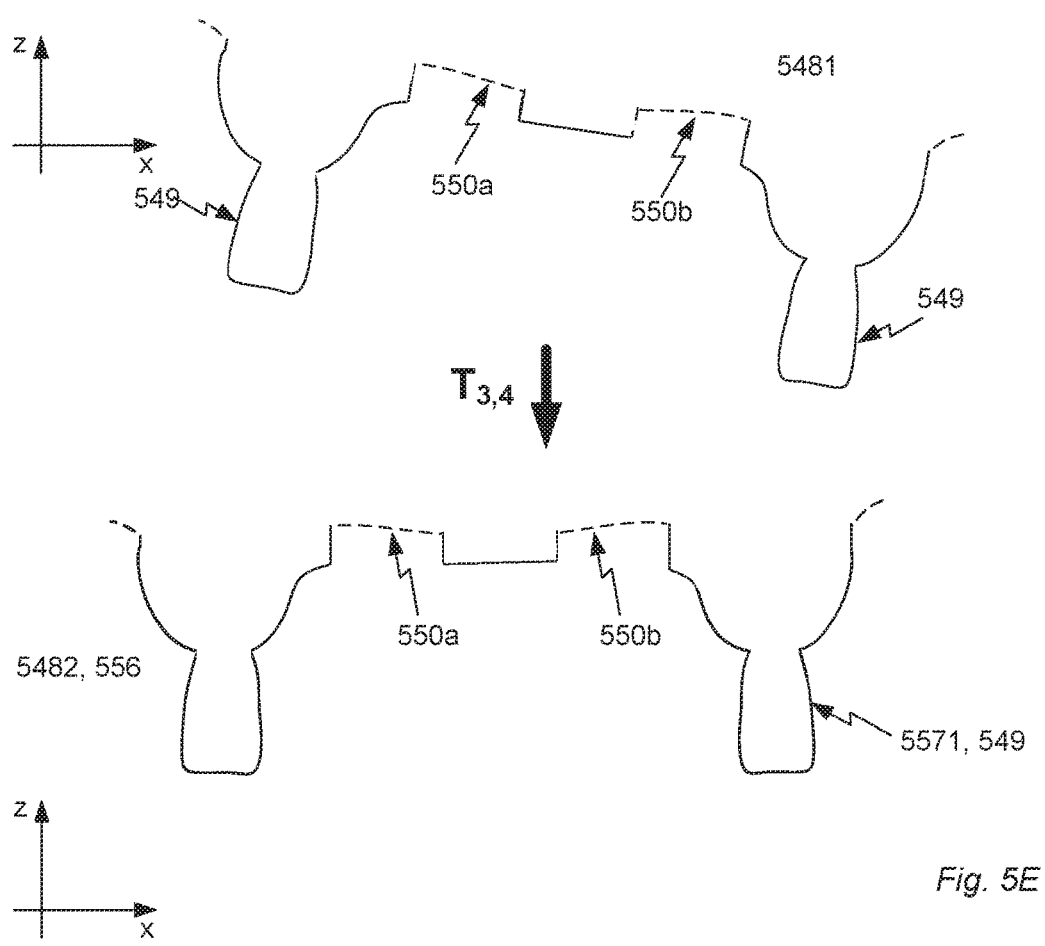

FIG. 5E illustrates that applying a second transformation matrix $T_{3,4}$ on the surface data 5481 of the third digital 3D representation has the effect that the transformed third digital 3D representation is rotated (relative to the coordinate system of the fourth digital 3D representation).

In addition to the surface data 550a, 550b relating to the visible dental tissue in the upper jaw, the third digital 3D representation also comprises surface data 549 relating to the first part of the scan appliance.

Figure 5F:
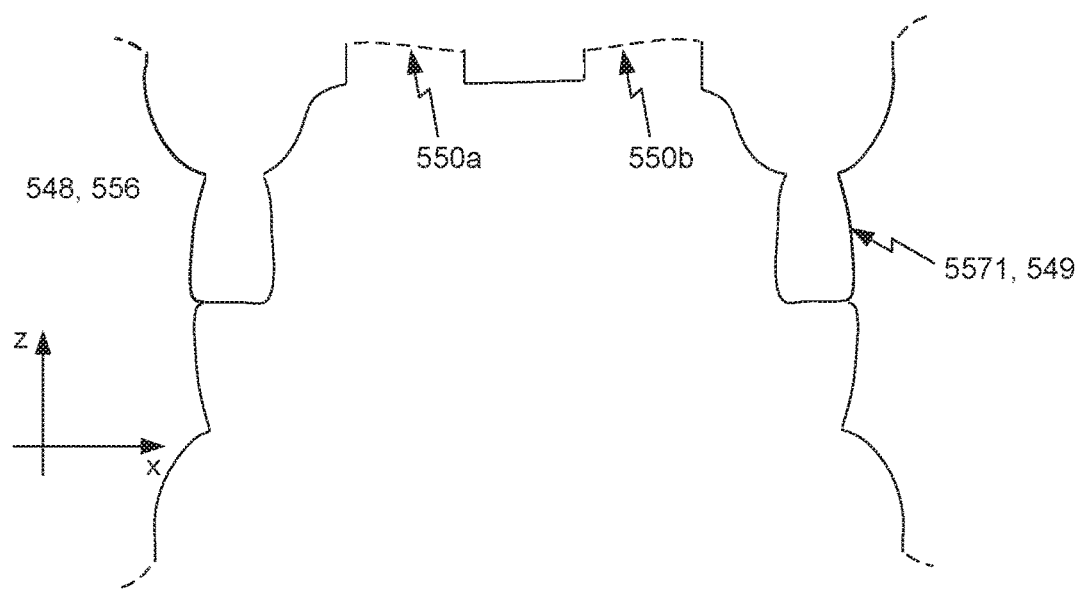
Figure 5G:
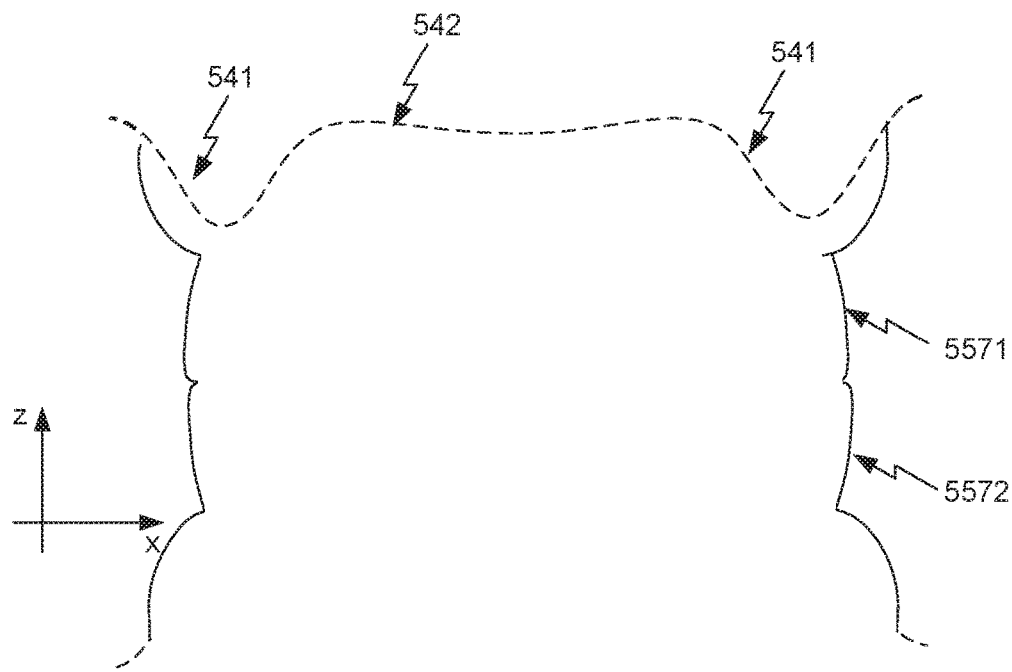

The second transformation matrix $T_{3,4}$ can then be determined using e.g. computer implemented Iterative Closest Point algorithms to align the surface data of the third and fourth 3D representations relating to the first scan appliance 549, 5571. Applying the second transformation matrix $T_{3,4}$ on the third digital 3D representation provides that the transformed third digital 3D representation is mapped into the coordinate system of the fourth digital 3D representation with the dental tissue surface data 550a, 550b arranged according to the situation in the bite position of the mandibular and maxillary dentures. I.e. the dental tissue surface data 550a, 550b of the third digital 3D representation is mapped into the coordinate system of the fourth digital 3D representation as illustrated in FIG. 5F. Applying first the $T_{1,3}$ and then the $T_{3,4}$ transformation matrices on the first digital 3D representation provides that the dental tissue surface data comprised therein are arranged correctly relative to the surface data 5571, 5572 of the fourth digital 3D representation. This may also be referred to as the transformed first digital 3D representation has been mapped into the coordinate system of the fourth digital 3D representation. The dental tissue surface data, e.g. the alveolar ridge surface data 541 and surface data palette 542, of the first digital 3D representation are then arranged relative to the scan appliance surface data 5571, 5572 of the fourth digital 3D representation according to their physical placement in the bite position as illustrated in FIG. 5G.

Transformation matrices for mapping the dental tissue surface data of the second digital 3D representation into the coordinate system of the fourth digital 3D representation can be determined in the same manner as those for the mapping of the first digital 3D representation. A $T_{2,5}$ transformation matrix for arranging the second digital 3D representation relative to the fifth digital 3D representation can be derived by aligning surface data corresponding to the same dental tissue in the lower jaw in a similar manner to the determining of $T_{1,3}$ above. Also in the same manner described above a $T_{5,4}$ transformation matrix for arranging the fifth and fourth digital 3D representations is derived by aligning the surface data for the second part of the scan appliance comprised in both these digital 3D representations.

The combined effect of applying first the $T_{2,5}$ and subsequently the $T_{5,4}$ transformation matrices to the second digital 3D representation is that the dental tissue surface data of the transformed second digital 3D representation are mapped into the coordinate system of the fourth digital 3D representation, i.e. the transformed second digital 3D representation is arranged correctly relative to the surface data of the fourth digital 3D representation. In other words, a third transformation matrix $T_{2,4}$ can hence be derived by from the $T_{2,5}$ and $T_{5,4}$ transformation matrices, where the third transformation matrix when applied to the second digital 3D representation provides that relative arrangement of the surface data of the fourth digital 3D representation and the transformed second digital 3D representation is according to the physical arrangement of the corresponding surfaces in the patient's mouth.

Figure 5H:
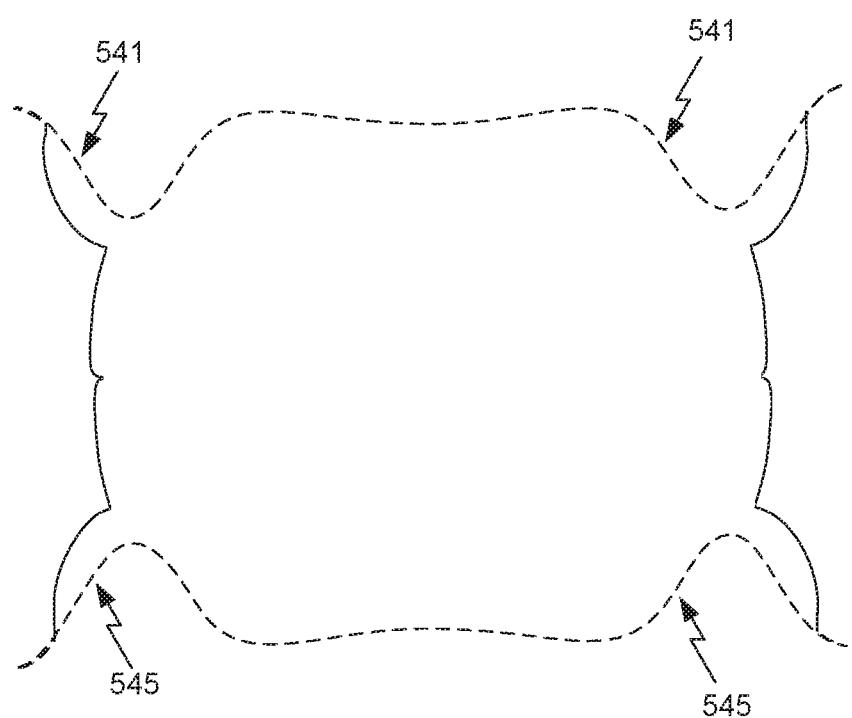

The result obtained when applying the $T_{2,5}$ and $T_{5,4}$ transformation matrices to the second digital 3D representation and the $T_{1,3}$ and $T_{3,4}$ transformation matrices to the first digital 3D representation is that these two digital 3D representations are arranged relative to each other according to their relative arrangement in the bite position defined by the dentures as illustrated in FIG. 5H. The surface data 541, 545 relating to the alveolar ridges of the upper and lower jaws are hence arranged according to their position in the patient's bite. FIG. 5H illustrates the result of the procedure. The dental tissue surface data for the upper and lower jaws are now mapped into a common coordinate system (the coordinate system of the fourth digital 3D representation) such that the relative arrangement of patient's jaws in the bite position is determined for this edentulous patient.

The transformations can also be derived and applied to provide that the first digital 3D representation is transformed to be arranged correctly relative to the second digital 3D representation or vice versa that the second digital 3D representation is transformed to be arranged correctly relative to the first digital 3D representation.

Figure 6:
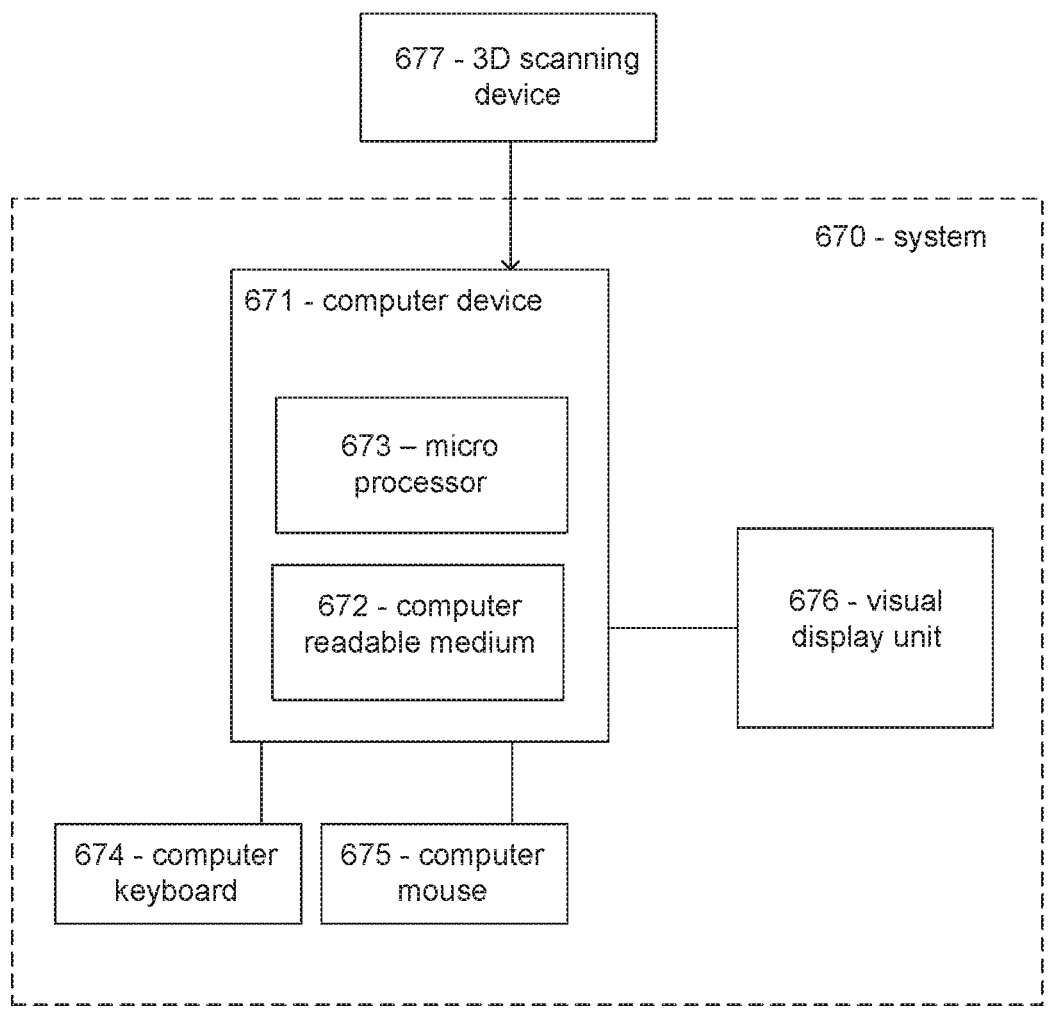
FIG. 6 shows a schematic of a system.

FIG. 6 shows a schematic of a system according to an embodiment of the present invention. The system 670 comprises a computer device 671 comprising a computer readable medium 672 and a processor 673. The system further comprises a visual display unit 676, a computer keyboard 674 and a computer mouse 675 for entering data and activating virtual buttons visualized on the visual display unit 676. The visual display unit 676 can be a computer screen. The computer device 671 is capable of receiving a digital 3D representation of the patient's oral cavity, recorded with or without a scan appliance arranged at the dental tissue, from a scanning device 677, such as the TRIOS intra-oral scanner manufactured by 3 shape A/S, or capable of receiving scan data from such a scanning device and forming a digital 3D representation of the patient's dental tissue and/or a scan appliance based on such scan data. The received or formed digital 3D representation can be stored in the computer readable medium 672 and provided to the processor 673. The processor 673 is configured for determining the relative arrangement of the patient's jaws in a bite position defined at least partly by the scan appliance. The relative arrangement can be determined by mapping a first and a second digital 3D representation of the patient's upper and lower jaws into the same coordinate system at least partly based on a digital 3D representations containing surface data for both the scan appliance and the dental tissue of the jaw where it is situated using the method according to any of the embodiments. The mapping may be realized by determining the transformation matrices required for bringing surface data of the first and second digital 3D representations into the common coordinate system.

The computer readable medium 672 can store algorithms configured for distinguishing between the scan appliance and the dental tissue based on color data of the digital 3D representations. When the scan appliance is made in a color different from that of the dental tissue in the patient's mouth, the computer device can then automatically identify which parts of a digital 3D representation relate to e.g. dental tissue and the transformation matrices.

The scanning of the patient's set of teeth using the scanning device 677 can be performed at a dentist while the designing of the dental restoration is performed at a dental laboratory. In such cases the recorded digital 3D representation can be provided via an internet connection between the dentist and the dental laboratory.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for determining the relative arrangement of patient's jaws in a bite position when the patient's occlusion is not defined by natural teeth alone, the method comprising:

obtaining, from an intra-oral scanner, a first digital 3D representation comprising surface data relating to dental tissue in a first one of the patient's jaws;

obtaining, from an intra-oral scanner, a second digital 3D representation comprising surface data relating to dental tissue in a second one of the patient's jaws;

obtaining, from an intra-oral scanner, a third digital 3D representation comprising both surface data relating to the dental tissue in the first one of the patient's jaws and surface data relating to a first part of a scan appliance arranged in relation to the first one of the patient's jaws, where the first part of the scan appliance is configured for at least partly defining the patient's occlusion in collaboration with an opposing structure at the second one of the patient's jaws, and where the first part of the scan appliance comprises one or more openings such that the dental tissue otherwise hidden by the scan appliance can be acquired by the intra-oral scanner while the first part of the scan appliance is placed at the first one of the patient's jaws;

obtaining a fourth digital 3D representation comprising surface data of the first part of the scan appliance and surface data relating to the opposing structure; and deriving one or more transformations for mapping the first digital 3D representation and second digital 3D representation into the same coordinate system with a relative arrangement according to the relative arrangement of the patient's jaws in the bite position.

2. The method according to claim 1, wherein a first one of the one or more transformations is derived at least partly based on dental tissue surface data of the third digital 3D representation recorded through the one or more openings in the first part of the scan appliance and on the corresponding dental tissue surface data of the first digital 3D representation.

3. The method according to claim 2, wherein a second one of the one or more transformations is derived at least partly based on scan appliance surface data of the third digital 3D representation and fourth digital 3D representation.

4. The method according to claim 3, wherein a third one of the one or more transformations is configured for transforming the second digital 3D representation and/or the fourth digital 3D representation to provide that the relative arrangement of the surface data of the second digital 3D representation and fourth digital 3D representation is according to the physical arrangement of the corresponding surfaces in the patient's mouth.

5. The method according to claim 4, wherein the opposing structure at least partly is defined by a second part of the scan appliance arranged in relation to the second one of the patient's jaws.

6. The method according to claim 5, wherein the second part of the scan appliance comprises one or more openings through which surface data for dental tissue of the second one of the patient's jaws can be recorded.

7. The method according to claim 6, wherein the method comprises obtaining a fifth digital 3D representation comprising both surface data relating to the dental tissue in the second one of the patient's jaws recorded though the one or more openings in the second part of the scan appliance and surface data relating to the second part of the scan appliance.

8. The method according to claim 7, wherein the third one of the transformations comprises a transformation configured for transforming the second digital 3D representation and/or the fifth digital 3D representation to provide that the second digital 3D representation and fifth digital 3D representation are arranged with aligned dental tissue surface data and a transformation configured for transforming the fourth and/or the fifth digital 3D representation to provide that the fourth digital 3D representation and fifth digital 3D representation are arranged with aligned scan appliance surface data.

9. The method according to claim 5, wherein the first part of the scan appliance and/or the second part of the scan appliance comprises a dental component from the group of:
  a denture,
  a copy of a denture,
  a try-in denture, or
  a bite rim.

10. The method according to claim 9, wherein one or more openings is defined by removing material of the scan appliance.

11. The method according to claim 4, wherein the opposing structure at least partly is defined by teeth of the second one of the patient's jaws, and at least part of the dental tissue surface data of the second digital 3D representation and of the fourth digital 3D representation relate to the teeth of the second one of the patient's jaws.

12. The method according to claim 11, wherein the third one of the transformations is configured to provide that at least part of the surface data of the second digital 3D representation and fourth digital 3D representation relating to the teeth in the second one of the patient's jaws are aligned.

13. The method according to claim 1, wherein the method comprises identifying portions of the third digital 3D representation relating to the first part of the scan appliance and identifying portions relating to the dental tissue in the first one of the patient's jaws.

14. The method according claim 13, where the first part of the scan appliance has a color which differs from the colors of the patient's dental tissue and wherein the identifying comprises executing computer implemented algorithms configured for distinguishing between the scan appliance and the dental tissue based on color data of the third digital 3D representation.

15. The method according to claim 13, wherein the identifying comprises digitally placing one or more sets of correlated digital alignment points on the third digital 3D representation and on the first digital 3D representation.

16. The method according to claim 1, wherein at least one of the one or more transformations comprises one or more transformation matrices.

17. The method according to claim 1, wherein the dental tissue surface data of the first digital 3D representation relates to the gum surface of the first one of the patient's jaws.

18. The method according to claim 1, wherein the dental tissue surface data of the second digital 3D representation relates to the gum surface of the second one of the patient's jaws.

19. A method for determining the relative arrangement of an edentulous patient's jaws in a bite position defined by the patient's existing dentures, the method comprising:
  obtaining, from an intra-oral scanner, a first digital 3D representation of the gums in the upper jaw;
  obtaining, from an intra-oral scanner, a second digital 3D representation of the gums in the lower jaw;
  obtaining, from an intra-oral scanner, a third digital 3D representation recorded with the patient's existing upper denture placed at the gums of the upper jaw, where one or more openings defined in the upper denture allows gum surface data to be recorded though the upper denture such that the third digital 3D representation comprises both surface data for the gums of the upper jaw and surface data for the upper denture;
  obtaining a fourth digital 3D representation comprising surface data for the upper and lower dentures and expressing the relative arrangement of the upper and lower dentures in the patient's bite; and
  deriving a plurality of transformations for mapping the first digital 3D representation and second digital 3D representation into the same coordinate system with a relative arrangement according to the relative arrangement of the patient's jaws in the bite position, where
    a first transformation of the plurality of transformations is derived by from gum surface data of the first digital 3D representation and third digital 3D representation, and
    a second transformation of the plurality of transformations is derived from denture surface data of the third digital 3D representation and fourth digital 3D representation,
wherein the method comprises obtaining a fifth digital 3D representation recorded with the patient's existing lower denture placed at the gums of the lower jaw, where one or more openings defined in the lower denture allows gum surface data to be recorded though the lower denture such that the fifth digital 3D representation comprises both surface data for the gums of the lower jaw and surface data for the lower denture, and a third transformation of the plurality of transformations is derived from gum surface data of the second digital 3D representation and fifth digital 3D representation.

20. The method according to claim 19, wherein the first transformation of the plurality of transformations at least partly is derived by aligning the gum surface data of the first digital 3D representation and third digital 3D representation.

21. The method according to claim 19, wherein the second transformation of the plurality of transformations at least partly is derived by aligning the gum surface data of the third digital 3D representation and fourth digital 3D representation.

\* \* \* \* \*